US011603564B2

(12) United States Patent
Torgersen et al.

(10) Patent No.: US 11,603,564 B2
(45) Date of Patent: Mar. 14, 2023

(54) HSMI DISEASE RESISTANCE IN SALMONIDS

(71) Applicant: AQUAGEN AS, Postboks (NO)

(72) Inventors: Jacob Seilø Torgersen, Ås (NO); Torkjel Bruheim, Trondheim (NO); Vibeke Evenstad Emilsen, Ranheim (NO); Thomas Moen, Aas (NO); Nina Santi, Trondheim (NO)

(73) Assignee: AQUAGEN AS, Postboks (NO)

( * ) Notice: Subject to any disclaimer, the term of this patent is extended or adjusted under 35 U.S.C. 154(b) by 206 days.

(21) Appl. No.: 16/481,807

(22) PCT Filed: Jan. 30, 2018

(86) PCT No.: PCT/GB2018/050252
§ 371 (c)(1),
(2) Date: Jul. 29, 2019

(87) PCT Pub. No.: WO2018/138527
PCT Pub. Date: Aug. 2, 2018

(65) Prior Publication Data
US 2020/0190584 A1    Jun. 18, 2020

(30) Foreign Application Priority Data
Jan. 30, 2017  (GB) ...................... 1701480

(51) Int. Cl.
*C12Q 1/6883*    (2018.01)
(52) U.S. Cl.
CPC ..... *C12Q 1/6883* (2013.01); *C12Q 2600/124* (2013.01); *C12Q 2600/156* (2013.01)
(58) Field of Classification Search
None
See application file for complete search history.

(56) References Cited

U.S. PATENT DOCUMENTS

2015/0329903 A1* 11/2015  Moen .................. C12Q 1/6874
506/2

FOREIGN PATENT DOCUMENTS

WO    2015104550 A1    7/2015
WO    2015104551 A1    7/2015

OTHER PUBLICATIONS

Lucentini et al The Scientist (2004) vol. 18, p. 20 (Year: 2004).*
Hirschhorn et al. Genetics in Medicine. vol. 4, No. 2, pp. 45-61, Mar. 2002 (Year: 2002).*
Leong et al. GenBank Accession No. BT046059, Aug. 24, 2010, NCBI, National Library of Medicine, available via URL: <.ncbi.nlm.nih.gov/nuccore/BT046059> (Year: 2010).*
Krasnov, Aleksei, et al. "Genomic survey of early responses to viruses in Atlantic salmon, *Salmo salar* L." Molecular immunology 49.1-2 (2011): 163-174.
Markussen, Turhan, et al. "Sequence analysis of the genome of piscine orthoreovirus (PRV) associated with heart and skeletal muscle inflammation (HSMI) in Atlantic salmon (*Salmo salar*)." PloS one 8.7 (2013): e70075.
EPO Examination Report, 18 703 817.9, pp. 1-7, dated Nov. 25, 2020.
Resistance against HSMI, XP-002779004, Feb. 2017, <https://aquagen.no/wp-content/uploads/2017/08/qt1-innova-eng.pdf>.
Kristoffersen et al, "Risk Mapping of Heart and Skeletal Muscle Inflammation in Salmon Farming", Preventive Veterinary Medicine, vol. 109. No. 1-2, Apr. 1, 2013, pp. 136-143, XP055458628.
Løvoll et al, "Quantification of Piscine Reovirus (PRV) at Different Stages of Atlantic *Salmon Salmo salar* Production", Diseases of Aquatic Organism, vol. 99, No. 1, May 15, 2012, pp. 7-12, XP055118450.
International Search Report, PCT GB2018/050252, pp. 1-2, dated Apr. 16, 2018.
Biering, E., and Å. H. Garseth. "Heart and skeletal muscle inflammation (HSMI) of farmed Atlantic salmon (*Salmo salar* L.) and the associated Piscine reovirus (PRV)." Copenhagen: International Council for the Exploration of the Sea (2012).
Chang et al. GIGA Science, "Second-generation PLINK: rising to the challenge of larger and richer datasets", pp. 1-16, 2015.
Cingolani et al, Landes Bioscience, "A program for annotating and predicting the effects of single nucleotide polymorphisms, SnpEff: SNPs in the genome of *Drosophia melanogaster* strain w1118; iso-2; iso-3", Fly 6:2, pp. 80-92, 2012.
Garrison and Marth, "Haplotype-based Variant Detection from Short-Read Sequencing", Jan. 12, 2016, pp. 1-20.
Gjedrem et al, Elsevier Science Publishers B.V. Amsterdam, "Genetic Origin of Norwegian Farmed Atlantic Salmon", Aquaculture, 98 (1991), pp. 41-50.
Godoy et al, "First Description of Clinical Presentation of Piscine Orthoreovirus (PRV) Infections in Salmonid Aquaculture in Chile and Identification of a Second Genotype (Genotype II) of PRF", Virology Journal (2016) 13:98.
Hjeltnes et al, "Fish Health Report 2015", Veterinaerinstituttet, Norewegian Veterinary Institute, Report 3B, 2016.
Kongtorp et al., "Heart and Skeletal Muscle Inflammation in Atlantic Salmon, *Salmo salar* L.: a new infectious disease", Journal of Fish Diseases 2004, 27, 351-358.

(Continued)

*Primary Examiner* — Carla J Myers
(74) *Attorney, Agent, or Firm* — Shook, Hardy & Bacon LLP

(57) ABSTRACT

The present invention relates to methods of predicting resistance to heart and skeletal muscle inflammation in salmonids, the method comprising determining the alleles present at a DNA polymorphism in the salmonid and predicting whether or not the salmonid is resistant to heart and skeletal muscle inflammation based on the determination of the alleles. The invention also relates to related methods of detecting, in a sample from a salmonid, the alleles present at a DNA polymorphism associated with resistance to heart and skeletal muscle inflammation, methods for obtaining an indication of risk of a salmonid developing heart and skeletal muscle inflammation, uses of such DNA polymorphisms, and methods of detecting, in a sample from a salmonid, one or more salmonid gene variants.

Figure 1:
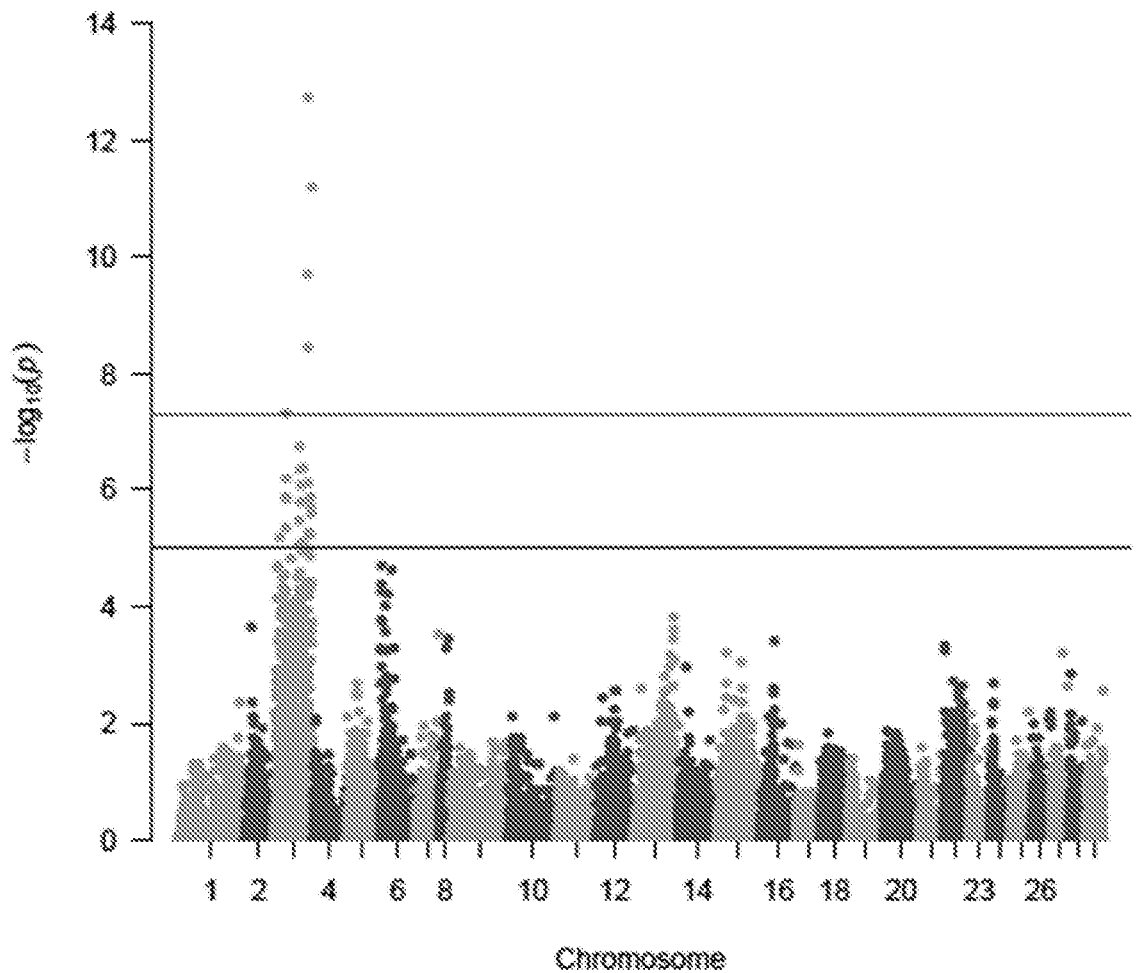

10 Claims, 3 Drawing Sheets
Specification includes a Sequence Listing.

(56) References Cited

OTHER PUBLICATIONS

Li and Durbin, "Fast and Accurate Short Read Alignment with Burrows-Wheeler Transform", Bioinformatics, vol. 25 No. 14 2009, pp. 1754-1760.
Olsen et al., "First Description of a New Disease in Rainbow Trout (*Oncorhynchus mykiss* (Walbaum)) Similar to Heart and Skeletal Muscle Inflammation (HSMI) and Detection of a Gene Sequence Related to Piscine Orthoreovirus (PRV)", PLoS One 10(7), Jul. 15, 2015.
Palacios et al., "Heart and Skeletal Muscle Inflammation of Farmed Salmon Is Associated with Infection with a Novel Reovirus", PLoS One 5(7), Jul. 9, 2010.
International Preliminary Report on Patentability received for PCT Application No. PCT/GB2018/050252, dated Aug. 8, 2019, 9 pages.
Intention to grant received for EP Patent Application No. 18703817.9, dated Jul. 27, 2021, 66 pages.
"Salmobase", Retrieved from Internet URL : https://salmobase.org, accessed on Sep. 13, 2022, pp. 3.
"Affymetrix", Axiom 2.0 Assay Manual Workflow, Retrieved from Internet URL : http://media. affymetrix.com/support/downloads/manuals/axiom_2 assay_manual_workflow_prepguide.pdf, pp. 1-12 (2013).
"Challenge models", Namsos, Retrieved from Internet URL : https://www.veso.no/challenge-models, accessed on Sep. 13, 2022, pp. 5.

* cited by examiner

HSMI DISEASE RESISTANCE IN SALMONIDS

CROSS-REFERENCE TO RELATED APPLICATIONS

This application claims priority under 35 U.S.C. § 365 to PCT/GB2018/050252, filed on Jan. 30, 2018, entitled "HSMI DISEASE RESISTANCE IN SALMONIDS," which claims priority to British App. No. 1701480.4 filed on Jan. 1, 2017, the entirety of the aforementioned applications are incorporated by reference herein.

The present invention relates to methods for predicting resistance to heart and skeletal muscle inflammation (HSMI) in salmonid fish, more specifically the invention relates to predicting such resistance by the analysis of DNA polymorphisms.

Heart and skeletal muscle inflammation is a disease that causes substantial economic loss and animal welfare problems within the aquaculture industry. Taking the farming of Atlantic salmon (Salmo salar) as an example, outbreaks of the disease can cause up to 20% mortality at affected sites. Morbidity is frequently close to 100%, resulting in under-sized fish and poor product quality. The disease has been diagnosed in Norway, Scotland, Ireland, Chile, and Canada based on histopathological analysis of heart and muscle tissue (Biering and Garseth 2012, Olsen et al. 2015, Godoy et al, 2016). In Norway alone, 135 outbreaks of the disease were recorded in 2015 (Hjeltnes et al. 2016). The aetiological agent is believed to be a recently discovered virus called Piscine Orthoreovirus (PRV) (Kongtorp et al. 2004; Palacios et al. 2010). Research has indicated that PRV enters the animal through the gut, and that it replicates in red blood cells and heart muscle. The disease is primarily a problem during the first 6 months after transfer to sea cages, but outbreaks have also been recorded in freshwater hatcheries that use seawater in their production. Outbreaks of HSMI, connected to PRV-like viruses, have for example been reported for Atlantic salmon (Biering and Garseth 2012, and references therein), for rainbow trout (Olsen et al. 2015) and coho salmon (Godoy et al. 2016).

A cure for HSMI has not yet been found, Commercial vaccines are not available. In general, vaccines for viral diseases in fish such as salmonids tend to have suboptimal efficacy (Hjeltnes et al. 2016).

In the absence of other means for combatting HSMI, selective breeding could be used in order to create fish with increased resistance to the disease. Selection of broodstock could, for example, be based on an experimental challenge test for assaying the resistance of individual animals to HSMI; such a test has been established by VESO Vikan (Namsos, Norway, www.veso.no). Using the test procedure, large groups of fish can be exposed to the virus through the use of pre-infected cohabitants. After a period of 6-10 weeks, samples are taken from each fish and used for measuring histopathology scores (semi-quantitative assessments of histopathological changes occurring because of infection) or expression levels of marker genes expressed by the virus or by the host (i.e. expression levels of genes that are turned on as a result of infection; quantified using quantitative PCR, qPCR). One problem with the approach is that the required tissue samples cannot be taken without killing the animal, so that tested animals are lost as broodstock candidates. Also, even if samples could be taken from live animals, challenge-tested animals could not be used as broodstock due to the risk of vertical transmission of the disease. The typical solution to this problem is to sample broodstock among siblings of the challenge-tested animals, i.e. use as broodstock untested, random, representatives of the best-performing sibling groups. This approach is often referred to as 'family selection', and it exploits only 50% of the potential for genetic improvement (it makes no allowance for the within-family component of genetic variation, constituting 50% of the total genetic variance on average).

If other phenotypes correlated to HSMI resistance could be found, and if these phenotypes could be measured directly on broodstock candidates, then both the between- and within components of genetic variation could be exploited, resulting in faster genetic improvement. Relative to the family selection scheme laid out above, the use of such measurements would, in addition, have the benefit of not requiring breeding candidates to have close relatives with phenotypes, or to be sacrificed.

There is therefore a need for alternative methodologies for assaying animals' resistance to heart and skeletal muscle inflammation; particularly methodologies that allow direct assaying of individual's resistance to heart and skeletal muscle inflammation, whilst retaining the possibility of using the tested animal as broodstock. As part of this need, there is a need for novel markers for assaying animals' resistance to heart and skeletal muscle inflammation.

The inventors of the present invention have, following extensive experimentation, identified that one can predict resistance to heart and skeletal muscle inflammation in salmonids by analysis of one or more DNA polymorphisms (thereby satisfying the aforementioned need).

Accordingly, in a first aspect of the present invention, there is provided a method of predicting resistance to heart and skeletal muscle inflammation in salmonids, the method comprising determining the alleles present at a DNA polymorphism in the salmonid and predicting whether or not the salmonid is resistant to heart and skeletal muscle inflammation based on the determination of the alleles.

In a further aspect, there is provided a method of detecting, in a sample from a salmonid, the alleles present at a DNA polymorphism associated with resistance to heart and skeletal muscle inflammation. The presence of the DNA polymorphism may be indicative of the salmonid being resistant to heart and skeletal muscle inflammation. The method may comprise detection of the allele in the sample and wherein the detection confirms the presence or absence of the allele in the sample. The method may comprise any known method of detecting the alleles in the sample, many of which are described below, for example by sequence analysis.

In a further aspect, there is provided a method for obtaining an indication of risk of a salmonid developing heart and skeletal muscle inflammation, the method comprising: detecting, in a sample from the salmonid, the alleles present at a DNA polymorphism associated with resistance to heart and skeletal muscle inflammation, wherein the presence of the DNA polymorphism is indicative of the salmonid being resistant to heart and skeletal muscle inflammation.

In a further aspect, there is provided a use of a DNA polymorphism, associated with resistance to heart and skeletal muscle inflammation, for detecting salmonid being resistant to heart and skeletal muscle inflammation.

In a further aspect, there is provided a method of detecting, in a sample from a salmonid, one or more salmonid gene variants in the locus defined by position 78,364,536 bp to 91,273,924 bp in the Atlantic salmon genome; and assaying the sample to detect the one or more salmonid gene variants, the one or more salmonid gene variants selected from one or more of the DNA polymorphisms listed in Tables 1 to 6.

The inventors have found that the DNA polymorphisms of the present invention can be present in either of two forms, i.e. the DNA polymorphisms have two alleles. One allele can be characterised as being predictive of resistance to heart and skeletal muscle inflammation (i.e. the resistance allele); the other being predictive of non-resistance to heart and skeletal muscle inflammation (i.e. non-resistance allele). Salmonids are diploid organisms, and so possess two copies of the polymorphisms of the present invention (one copy to be found in each set of chromosomes). The step of determining the alleles in the method of the first aspect of the present invention therefore includes the step of analysing the DNA polymorphism provided in each set of chromosomes in order to determine whether each copy of the DNA polymorphism present is a resistance allele or is a non-resistance allele. When a salmonid subjected to the method of the present invention is determined to have two copies of the resistance allele for the DNA polymorphism (i.e. the salmonid is homozygous for the resistance allele), the salmonid is predicted to have resistance to heart and skeletal muscle inflammation. Conversely, when a salmonid subjected to the method of the present invention is determined to have two copies of the non-resistance allele for the DNA polymorphism (i.e. is homozygous for the non-resistance allele), the salmonid is predicted not to have resistance to heart and skeletal muscle inflammation. It may be concluded that a salmonid that is predicted by the method of the present invention as having heart and skeletal muscle inflammation resistance has a greater than normal chance of having heart and skeletal muscle inflammation resistance. Conversely, it may be concluded that a salmonid that is predicted not to have heart and skeletal muscle inflammation resistance has a lower than normal risk of developing heart and skeletal muscle inflammation resistance. When a salmonid subjected to the method of the present invention is determined to have one copy of the resistance allele for the DNA polymorphism and one copy of the non-resistance allele for the DNA polymorphism (i.e. is heterozygous), the salmonid would not be predicted according to the present invention to have resistance to heart and skeletal muscle inflammation. However, that salmonid would be predicted to have a greater chance of being resistant to heart and skeletal muscle inflammation than a salmonid with two copies of the non-resistance allele. Henceforth, such a salmonid will be referred to as having semi-resistance to heart and skeletal muscle inflammation.

The DNA polymorphism in question can be any of several DNA polymorphisms found by the inventor to have this predictive ability. The DNA polymorphisms of the present invention may be located on Atlantic salmon chromosome 3 or 14, or a combination thereof, or on an orthologous chromosome or combination thereof in another salmonid. The DNA polymorphisms are linked by locus in the fish genome and by their ability to predict resistance to heart and skeletal muscle inflammation.

The DNA polymorphism may be a single nucleotide polymorphism (SNP), a multiple nucleotide polymorphism, an addition mutation, or a deletion mutation. Each type of DNA polymorphism provided above is contemplated individually as part of the present invention for the step of determining in the methods of the present invention.

The DNA polymorphisms may be located in the region extending from position 78,364,536 bp to 91,273,924 bp in Atlantic salmon, chromosome 3 (GenBank identifier NC_027302.1), or corresponding region of the relevant salmonid.

The DNA polymorphism may be selected from any one or more of the DNA polymorphisms provided in Table 1. Each of the DNA polymorphisms provided in Table 1 is contemplated individually as part of the present invention.

The DNA polymorphism may be selected from any one or more of the DNA polymorphisms provided in Table 2. Each of the DNA polymorphisms provided in Table 2 is contemplated individually as part of the present invention.

The DNA polymorphism may be selected from any one or more of the DNA polymorphisms provided in Table 3. Each of the DNA polymorphisms provided in Table 3 is contemplated individually as part of the present invention.

The DNA polymorphism may be selected from any one or more of the DNA polymorphisms provided in Table 4. Each of the DNA polymorphisms provided in Table 4 is contemplated individually as part of the present invention.

The DNA polymorphism may be selected from any one or more of the DNA polymorphisms provided in Table 5. Each of the DNA polymorphisms provided in Table 5 is contemplated individually as part of the present invention.

The DNA polymorphism may be selected from any one or more of the DNA polymorphisms provided in Table 6. Each of the DNA polymorphisms provided in Table 6 is contemplated individually as part of the present invention.

The DNA polymorphism may be selected from polymorphism No. 1 or 9, or both.

Each of these DNA polymorphisms is contemplated individually as part of the present invention.

The DNA polymorphism may be selected from any one or more of polymorphism Nos. 1, 2, 7 and 9, and any combination thereof. Each of these DNA polymorphisms is contemplated individually as part of the present invention.

The DNA polymorphism may be selected from any one or more of polymorphism Nos. 1, 2, 7, 9, 13, 14, 15 and 16, and any combination thereof. Each of these DNA polymorphisms is contemplated individually as part of the present invention.

The method may employ one or more of the polymorphisms provided in Table 1, 2, 3, 4, 5, 6 and one or more additional polymorphism, or any combination thereof.

As discussed, each of the above DNA polymorphisms is contemplated individually as part of the present invention. Consequently, any one or combination of the aforementioned DNA polymorphisms may be extracted from the lists and used in the present invention. Indeed, the methods of the present invention may involve the determination of alleles present in any one or more of the polymorphism described above, in addition to any further polymorphisms that are predictive for HSMI.

The method may employ two or more of any of the polymorphisms discussed above, for example as provided in Table 1, 2, 3, 4, 5, 6, or any combination thereof.

When the method is employed with two DNA polymorphisms, the two DNA polymorphisms could constitute one unit, hereafter referred to as a haplotype. Each haplotype can have four different alleles, corresponding to the four different combinations of DNA polymorphism alleles at the individual DNA polymorphisms (for example, if the haplotype is made up of one DNA polymorphism with alleles A and T, and one DNA polymorphisms with alleles T and G, the four possible haplotype alleles are A-T, A-G, T-T, and T-G). Each of these four alleles would be either a resistance allele or a non-resistance allele, in a manner analogous to the single DNA polymorphism method laid out above. Thus, in the hypothetical case of a haplotype having the four alleles A-T, A-G, T-T, and T-G, it could be that all A-T, A-G, and T-T were resistance alleles, whereas T-G was a non-resistance allele. In that case, an animal having one copy of the A-T allele and one copy of the A-G allele would be resistant to heart and skeletal muscle inflammation, an animal having one copy of A-T and one copy of T-G would be semi-resistant, while an animal having two copies of T-G would be non-resistant.

When the method is employed with three or more DNA polymorphisms, the three or more DNA polymorphisms could constitute a haplotype in a manner analogous to the situation described for two DNA polymorphisms.

All methods described herein may be applied to any salmonid, i.e. to any species within the family of Salmonidae. Examples of such species are Atlantic salmon (i.e. *Salmo salar*), rainbow trout (i.e. *Oncorhynchus mykiss*), and coho salmon (i.e. *Oncorhynchus kisutch*).

The step of determining the presence or absence in a salmonid may be practised on a sample taken from the salmonid. The sample may be any sample in which analysis of nucleic acid material is possible, as would be readily understood by the person skilled in the art. For the avoidance of doubt, the sample may be a skeletal muscle tissue sample, blood sample, liver sample, heart sample and/or a fin clip.

The skilled person would be well aware of all available methods capable of testing for the presence or absence of DNA polymorphism alleles, i.e. for the genotyping of a DNA polymorphism in an individual salmon (or other organisms).

For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), competitive hybridisation of probes complementary to the different alleles (e.g. the TaqMan assay from Applied Biosystems), assays combining DNA ligation with DNA hybridisation (Axiom technology from Affymetrix), or genotyping-by-sequencing, e.g., deduction of genotypes from next-generation sequencing data (such as Illumina HiSeq data).

Not wishing to be restricted further, but for clarity, techniques such as Axiom from Affymetrix can involve the following: DNA is amplified and fragmented, then denatured. The DNA fragments ('template DNA') are hybridised to a microarray. Every spot on the microarray corresponds to one particular SNP, and each spot contains (covalently bound to the array surface) oligonucleotides which are complementary to one of the flanks of the SNP in question; consequently, the template DNA will hybridise to these microarray-bound oligonucleotides. Next, free oligonucleotides, fluorescently labelled in one end and containing at the other end either of the two nucleotides possible at the SNP in question, are added to the mix. The recently added free oligonucleotide will hybridise to the template fragment, whereupon DNA ligation will be used in order to connect the recently added oligonucleotide to the oligonucleotide which is attached to the array. DNA ligation will only occur if the SNP nucleotide at the template fragment is complementary to the SNP nucleotide at the free nucleotide, i.e. it is the DNA ligation step which determines specificity. The identity of the free oligonucleotide which ends up being ligated to the array-bound oligonucleotide can be 'read' because each of the two different free oligonucleotides, having different SNP nucleotides, has a separate fluorescence molecule linked to it (i.e. in the end the results is read as a fluorescent signal).

Techniques such as iPlex from Agena Bioscience can involve the following: DNA is PCR-amplified. After amplification comes a primer extension step, wherein chain elongation is terminated using dideoxynucleotides; ddX, where X can be one or more nucleotides. Thus, for each SNP two different oligonucleotides are produced; these differ due to the identity of the last nucleotide of the chain. The oligonucleotide fragments are detected using time-of-flight mass spectroscopy.

Techniques such as DNA sequencing (eg Genotyping by sequencing) can involve the following: DNA is sequenced using next-generation sequencing or Sanger sequencing. The resulting DNA fragments are aligned to a template, whereupon algorithms are used in order to deduce a genotype on the basis of all the DNA 'reads' aligned to the SNP position Consequently, in a further aspect of the present invention, there is provided a hybridisation probe that is specific for one or more of the aforementioned DNA polymorphisms.

The DNA sequence at and around the DNA polymorphisms can be found in Table 6. Also, the DNA sequence at and around the DNA polymorphism can be found in the dbSNP database, a partition of the GenBank (www.ncbi.nlm.nih.gov). Using the published version of the Atlantic salmon genome sequence, and the sequences of DNA polymorphisms provided in Table 6 or the Atlantic salmon genome coordinates provided in Table 1, 2, 3, or 4, the skilled person can, if necessary, extend the sequences around any DNA polymorphism of the invention to any required length. The DNA sequence of the Atlantic salmon genome is available on GenBank (accession number GCA_000233375.4).

The sequence can also be browsed at the website of the consortium that sequenced the Atlantic salmon genome; www.salmobase.org).

Hybridisation probes that are selective for the DNA sequences in Table 6 may form part of the present invention.

A salmonid that is predicted to have resistance to heart and skeletal muscle inflammation according to the first aspect of the present invention is more likely than normal to produce offspring that have a higher than normal chance of having resistance to heart and skeletal muscle inflammation. Consequently, in a further aspect of the present inventions, there is provided a method of selecting a salmonid for use as broodstock, wherein the salmonid is selected, based on the prediction by the method as claimed in the first aspect of the present invention, to have resistance to heart and skeletal muscle inflammation.

Conversely, a salmonid predicted by the method of the first aspect of the present invention as not having resistance to heart and skeletal muscle inflammation would not be selected as broodstock.

In a further aspect of the present invention, there is provided a method of producing offspring that have a higher than normal chance of having resistance to heart and skeletal muscle inflammation, the method comprising:

detecting, in a sample from a salmonid, the alleles present at a DNA polymorphism associated with resistance to heart and skeletal muscle inflammation, wherein the presence of the DNA polymorphism is indicative of the salmonid being resistant to heart and skeletal muscle inflammation; and using the salmonid being resistant to heart and skeletal muscle inflammation to produce offspring.

The invention may also include the offspring produced according to this method.

In a further aspect of the present invention, there is provided a method of producing eggs that have a higher than normal chance of producing offspring from fertilisation of that egg that have resistance to heart and skeletal muscle inflammation, the method comprising:

detecting, in a sample from a salmonid, the alleles present at a DNA polymorphism associated with resistance to heart and skeletal muscle inflammation, wherein the presence of the DNA polymorphism is indicative of the salmonid being resistant to heart and skeletal muscle inflammation; and using the salmonid being resistant to heart and skeletal muscle inflammation to provide the eggs.

The present invention may also include the eggs produced according to this method.

The polymorphisms, including selections and combinations thereof, as discussed above may be those referred to in any of the aspects of the present invention.

The present invention also relates to an isolated polynucleotide comprising one or more of the DNA polymorphisms selected from the group provided above and located within a portion of the salmon genome. Exemplary sequences for such isolated polynucleotides may be found in Table 6.

The terms "haplotype", "haplotype allele" and "DNA polymorphism allele" take their normal meanings as would be well understood by the skilled person in the art. However, for the avoidance of doubt, "DNA polymorphism allele" may mean one of two different nucleotide sequences at the site of a DNA polymorphism of the present invention (one allele being the "resistant allele", the other being the "non-resistant allele"). By "haplotype" is meant a set of closely linked DNA polymorphism (located close to each other on one and the same chromosome) that are for the most part inherited as a block (i.e. without recombination) from parents to offspring. By "haplotype allele" is meant a combination of alleles from the DNA polymorphisms constituting a haplotype, such as would be found on a single chromosome copy within a diploid animal.

Hearth and Skeletal Muscle Inflammation (HSMI) is a well characterised and understood clinical disorder and as such would be understood by the person skilled in the art. As the person is aware that this disorder may be caused by viral infection, the person would be aware that the disorder predicted by the present invention may be virally induced HSMI (e.g. induced by PRV). As a consequence of this, the methods of the present invention encompass methods of predicting PRV infection.

The present invention will now be described by way of example with reference to the accompanying figures, in which:—

FIG. 1 displays a Manhattan plot coming from a genome-wide association study (GWAS) searching for DNA polymorphisms associated to histopathology score (being a proxy phenotype for heart and skeletal muscle inflammation) in Atlantic salmon. Positions along the x-axis are positions of the DNA polymorphisms relative to the published version of the Atlantic salmon genome (GenBank identifier=GCA_000233375.4), positions along the y-axis are −log 10 of the p-value of the GWAS LRT statistic.

Figure 2:
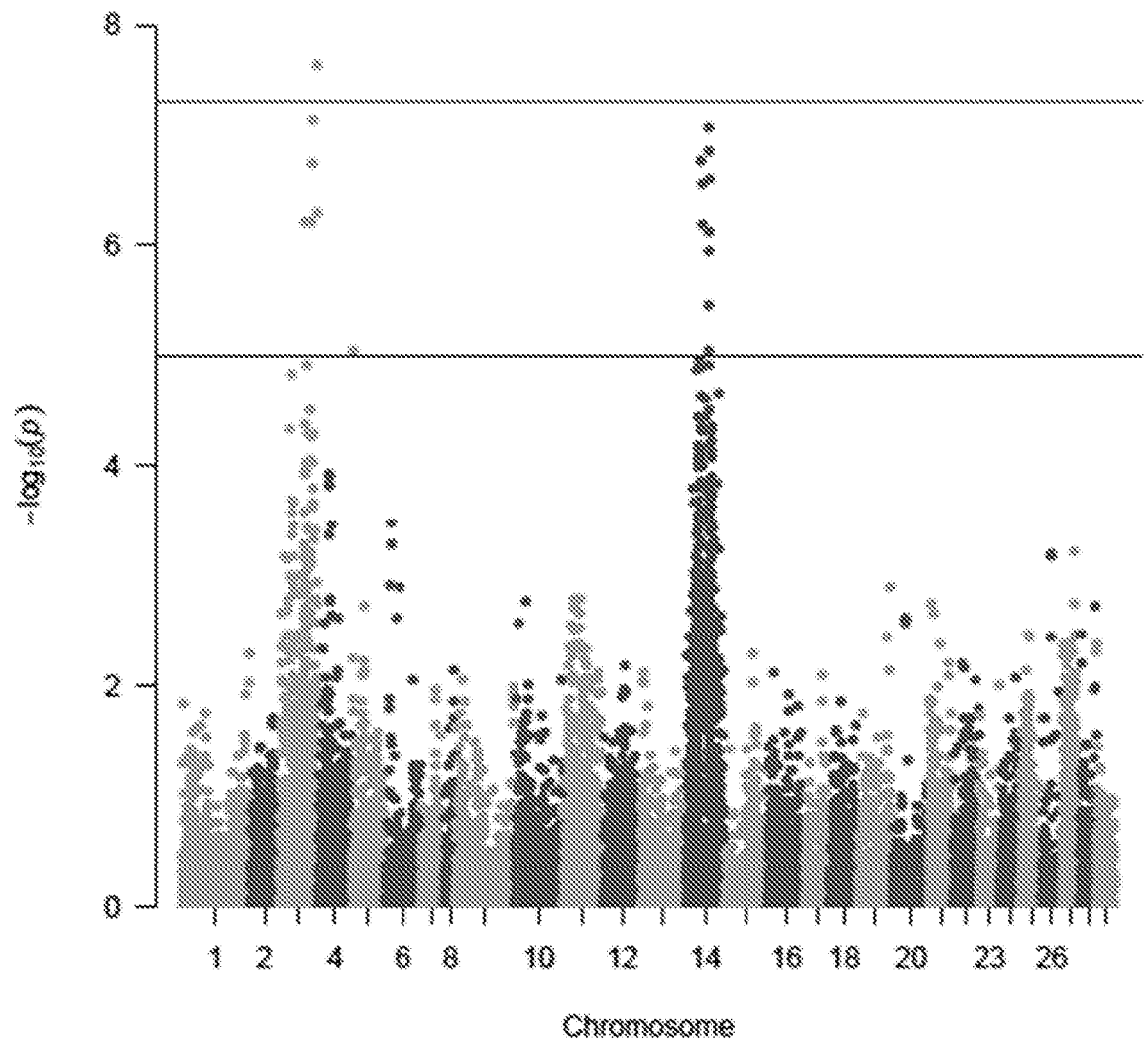

FIG. 2 displays a Manhattan plot coming from a genome-wide association study (GWAS) searching for DNA polymorphisms associated to cd8-qPCR values (being a proxy phenotype for heart and skeletal muscle inflammation) in Atlantic salmon. Positions along the x-axis are positions of the DNA polymorphisms relative to the published version of the Atlantic salmon genome (GenBank identifier=GCA_000233375.4), positions along the y-axis are −log 10 of the p-value of the GWAS LRT statistic.

Figure 3:
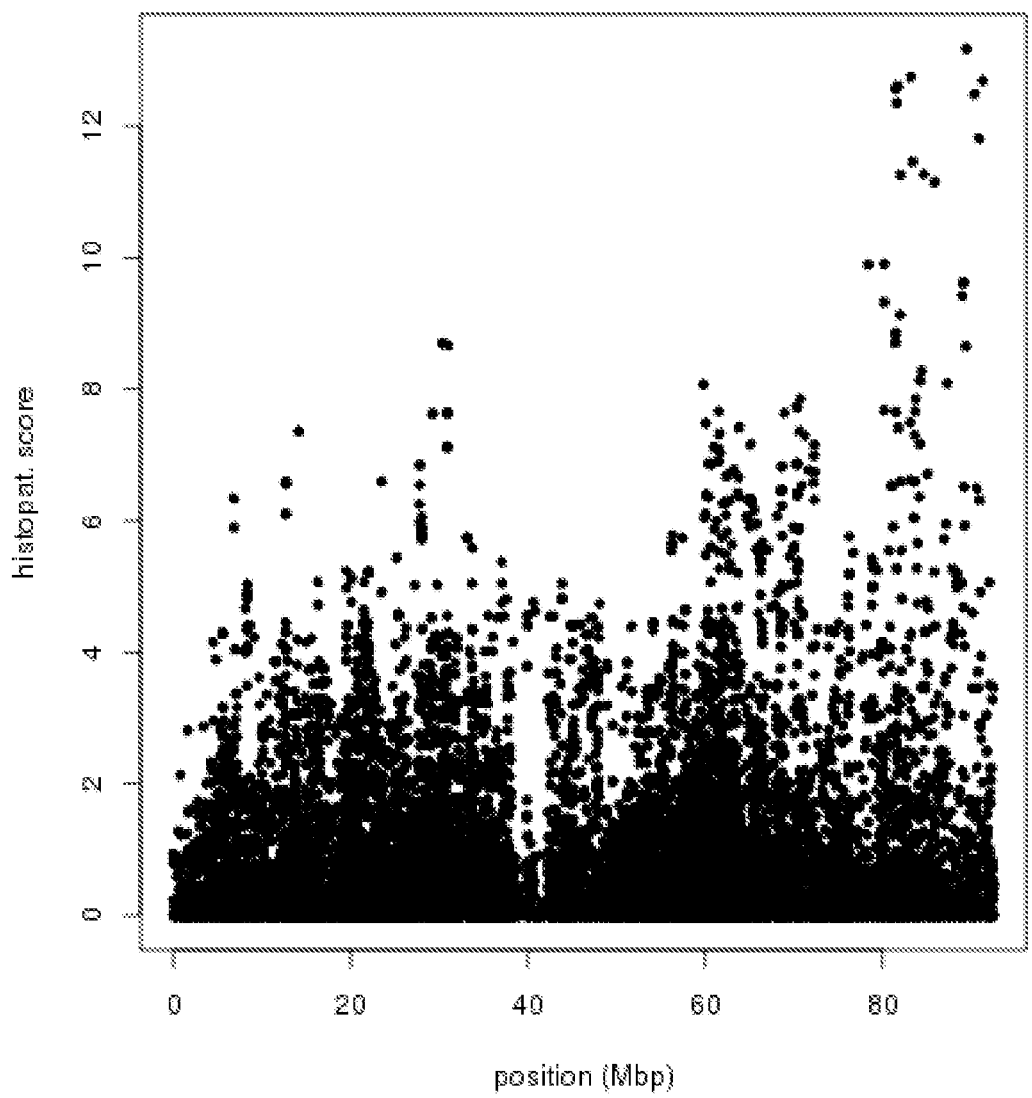

FIG. 3 displays a Manhattan plot coming from a genome-wide association study (GWAS) carried out on imputed data set, focusing on Atlantic salmon chromosome 3. Positions along the x-axis are positions of the DNA polymorphisms relative to the published version of Atlantic salmon chromosome 3 (GenBank identifier=NC_027302.1), positions along the y-axis are −log 10 of the p-value of the GWAS LRT statistic.

1. CHALLENGE TRIAL

The challenge trial was conducted as a cohabitant challenge at VESO Vikan (Namsos, Norway). A total of 1351 Atlantic salmon (*Salmo salar*) smolts of an average weight of 83 grams were included in the test. The smolts were recruited form 507 families in the AquaGen breeding nucleus. Each smolt had been tagged with Passive Integrated Transponder (PIT) tags prior to testing. Three hundred and four smolts were used as shedders. The shedders were injected with blood cells infected with PRV virus (from a clinical outbreak of HSMI in Nord-Trøndelag, Norway, in 2012). The AquaGen breeding nucleus of Atlantic salmon constitute a closed population of Atlantic salmon, having been selectively been bred for traits desirable for aquaculture production (fast growth rate, late sexual maturation, resistance to particular diseases) for twelve generations. The base population consisted of wild Atlantic salmon collected from a large collection of Norwegian rivers (Gjedrem et al. 1991).

The challenge was performed in sea water with a fish density of 40-60 kg/m$^3$ and at a temperature of 12° C.±1° C. Mortalities were registered daily until the test was terminated at 10 weeks post challenge. At this point all test fish (N=887) were registered and sampled: From each fish a heart biopsy was taken and stored on RNAlater for subsequent quantitative PCR. From 240 fish, heart and skeletal muscle biopsies were taken and fixed in 10% buffered formalin for subsequent histopathology.

2. HISTOPATHOLOGY

Formalin-fixed samples were prepared for histological examinations by standard paraffin wax techniques and stained with haematoxylin and eosin (H&E stain).

Sections of cardiac and skeletal muscle tissue from individual fish were classified histologically based on the presence of mononuclear leukocyte infiltration and muscular degeneration and necrosis. The atrium, epicardium, compact and spongy layers of the ventricle and the endocardium were examined and evaluated. The findings were graded from 0-3 according to the following criteria:

| Score | Description |
|---|---|
| 0 | No pathological findings |
| 1 | Few focal lesions, slightly increased number of leukocytes |
| 2 | Several distinct lesions and moderate increase in numbers of leukocytes |
| 3 | Multifocal to confluent lesions and severe increase in number of leukocytes |

Histopathology scores are directly indicative of tissue damages caused by the disease. Thus, histopathology scores can be used as indicators of an individual's disease status and hence, in the context of a controlled challenge test, of an individual's resistance to the disease to which they were challenge-tested.

3. REVERSE TRANSCRIPTION QUANTITATIVE PCR (RT-QPCR)

In order to provide an alternative (less expensive) phenotype analysis for HSMI infection or resistance, expression (transcription) levels of the Atlantic salmon cluster of differentiation 8 (cd8) gene was measured using reverse transcription quantitative PCR. The gene product of the gene, Cd8, is a marker for cytoxic T-cells. Cytoxic T-cells are, on their side, markers of viral infection. RT-qPCR for cd8 was performed as follows:

Total RNA was purified with a RNeasy 96 Universal Tissue 8000 Kit using a Qiagen Biorobot Universal. Duplex real time PCR was performed using primers targeted against the Atlantic salmon cd8 alpha chain (forward primer: 5'TCGTGCAAAGTGGGAAAGGT 3' (SEQ ID NO: 127), reverse primer: 5' GGTGCCCAAACGATCAAATC 3' (SEQ ID NO: 128), TaqMan probe: 5' FAM-ACCCTACTG-CATCCTG-MGB 3' (SEQ ID NO: 129)) and the housekeeping gene elf1a (forward primer: 5'-TGC CCC TCC AGG ATG TCT AC-3' (SEQ ID NO: 130), reverse primer: 5'-CAC GGC CCA CAG GTA CTG-3' (SEQ ID NO: 131), TaqMan probe: VIC 5'-CCA ATA CCG CCG ATT TT-3' MGB (SEQ ID NO: 132)). Amplification was performed using Quanti-Tect Probe RT-PCR kit (Qiagen) on a Rotor-Gene Q 2 channel Real Time PCR Machine, 40 cycles of 95° C. 15 sec and 60° C. 60 sec.

4. GENOTYPING

All fish were genotyped using a custom Axiom®SNP genotyping array from Affymetrix (San Diego, Calif., USA), and that formed a SNP-chip containing 56,177 SNPs. Genotyping was done according to the Axiom 2.0 Assay Manual Workflow User Guide (media.affymetrix.com). Genotype calling was done using the Affymetrix Power Tools programs (www.affymetrix.com), according to "best practices" recommendations from Affymetrix (media.affymetrix.com). Samples displaying poor genotype quality metrics were culled according to the "best practices" recommendations from Affymetrix. The SNP-chip was proprietary of Aqua-Gen, and contained SNPs evenly distributed across the Atlantic salmon genome.

5. GENOME-WIDE ASSOCIATION STUDY (GWAS)

The genotype data were used for performing a genome-wide association study (GWAS). Each individual SNP was assayed for its association to two phenotypes: histopathology scores and concentrations of cd8 mRNA as measured using RT-qPCR (this phenotype will be referred to as cd8-qPCR). Both phenotypes were used as indicators of morbidity and/or mortality. After culling of individuals with poor genotype quality, 779 individuals remained that had both genotypes and phenotypes (histopathology scores, cd8-qPCR) connected to them. Each of the 56,177 genotyped SNPs were tested individually for their association to histopathology scores, cd8-qPCR, using a linear mixed model. When the phenotype was histopathology score, the linear mixed model for each SNP was $$y=\text{mean}+\text{animal}+\text{geno}+\text{error}$$

where y=histopathology score for the animal in question; mean=the overall mean across all animals; animal=the additive genetic value of the animal in question (random effect); geno=genotype at the SNP for the animal in question (random regression; coded as 0, 1, and 2 for one homozygous genotype, the heterozygous genotype, and the other homozygous genotype, respectively); error=residual error.

When the phenotype was cd8-qPCR, the linear mixed model for SNP i was $$y=\text{mean}+\text{plate}+\text{animal}+\text{geno}+\text{error}$$

where y=histopathology score; mean=the overall mean across all animals; plate=fixed effect of the sample plate on which the RNA sample corresponding to the animal in question was located; animal=the additive genetic value of the animal in question (random effect); geno=genotype at the SNP for the animal in question (random regression; coded as 0, 1, and 2 for one homozygous genotype, the heterozygous genotype, and the other homozygous genotype, respectively); error=residual error.

The linear mixed model equations were solved using the software DMU. The likelihood ratio test (LRT) statistic was used, equal to two times the natural logarithm of the ratio H1/H0, where H1 and H0 are the likelihoods under the alternative hypothesis (model incorporates geno) and the null hypothesis (model does not incorporate geno), respectively.

The GWAS results revealed that histopathology scores are largely explained by a quantitative trait locus (QTL) located on Atlantic salmon chromosome 3 (FIG. 1). A number of DNA polymorphisms located on chromosome 3 were found to be highly correlated to histopathology score.

The GWAS results further revealed that cd8-qPCR values are largely explained by a quantitative trait locus (QTL) located on Atlantic salmon chromosome 3 (FIG. 2). A number of DNA polymorphisms located on chromosome 3 were found to be highly correlated to cd8 transcription levels.

Since the QTL for histopathology score and the QTL for cd-qPCR are both located on chromosome 3, it is reasonable to hypothesise that the two QTL are in fact one and the same QTL, i.e. they are both caused by one and the same underlying causative mutation, mapping to a specific location on chromosome 3. This expectation was backed up by the observed, high (in absolute value) genetic correlation between the two traits within the data set (Pearson correlation coefficient±standard error=−0.91±0.16).

Table 1 contains DNA polymorphisms located on Atlantic salmon chromosome 3 that were found to be associated strongly to histopathology score and to cd8-qPCR. The table contains the positions of these DNA polymorphisms, the p-values of their LRT statistics, and the identity of the high-resistance and low-resistance alleles pertaining to each DNA polymorphism. The positions in Table 1 are relative to the published version of Atlantic salmon chromosome 3 (GenBank identifier NC_027302.1). The high-resistance alleles in Table 1 are the alleles that correlate to low histopathology scores and high cd8-qPCR values. Conversely, the low-resistance alleles in Table 1 correlate to high histopathology scores and low cd8-qPCR values. High histopathology scores signify large extent of tissue damage. Low cd8-cPCR signify high concentrations of cd8 mRNA. High histopathology scores and high concentrations of cd8 mRNA are signs of viral infection.

As can be seen from FIG. 2, a QTL for cd8-qPCR was also found on chromosome 14. A number of DNA polymorphisms located on chromosome 14 were found to be highly correlated to cd8-qPCR. Table 2 displays the positions of these DNA polymorphisms, the p-values of their LRT statistics, and the identity of the high-resistance and low-resistance alleles pertaining to each DNA polymorphism. The positions in Table 2 are relative to the published version of Atlantic salmon chromosome 14 (GenBank identifier NC_027313.1). The high-resistance alleles in Table 2 are the alleles that correlate to high cd8-qPCR values (signifying low concentrations of cd8 mRNA and hence low levels of viral infection), and the low-resistance alleles are the alleles that correlate to low cd8-qPCR values (signifying high concentrations of cd8 mRNA and hence high levels of viral infection). High concentrations of cd8 mRNA correlate to low resistance because they indicate that the animal has mounted an immune response to PRV present in the body as a result of infection. Conversely, low concentrations of cd8 mRNA correlate to high resistance because they indicate that the animal has not needed to host an immune response to PRV present in the body as a result of infection.

The DNA polymorphisms in Table 2 have low minor allele frequency (0.10 or smaller), meaning that one of the alleles at the quantitative trait locus on chromosome 14 has low frequency within the studied population. This is a likely reason why the quantitative trait locus on chromosome 14 did not turn up as highly (genome-wide) significant when histopathology score was used as trait; only 240 animals were phenotyped for histopathology score, and few of these 240 animals harboured the rare allele at the quantitative trait locus on chromosome 14 (hence there was very little statistical power to detect the quantitative trait locus on chromosome 14 when histopathology score was used as trait). In fact, the DNA polymorphisms in Table 2 are associated with histopathology score ($P<0.05$), but they are not genome-wide significant, i.e. they are not significant after multiple testing has been taken into account.

The GWAS was performed using a SNP-chip containing 56,177 DNA polymorphisms. These are just a small fraction of all the DNA polymorphisms that exist in the Atlantic salmon genome. In order to identify additional DNA polymorphism associated to histopathology scores and/or cd8-qPCR, we used the following approach: The parents (hereafter referred to as 'the parents') of the individuals that had been put through the HSMI test ('the offspring') were genotyped on an Affymetrix Axiom SNP-chip containing 745,999 DNA polymorphisms distributed across the Atlantic salmon genome. The DNA polymorphisms on this chip had earlier been identified by AquaGen researchers on the basis of Illumina whole-genome sequencing of 28 individual Atlantic salmon from AquaGen. The parental genotypes (29,879 DNA polymorphisms on chromosome 3) were combined with offspring genotypes (2,278 polymorphisms on chromosome 3, all of which were part of the larger (29,879 polymorphisms) subset), in order to impute genotypes on all 29,879 DNA polymorphisms onto the offspring. This was done using the software FImpute, using default settings. The pedigree linking the two generations was used in the FImpute analysis, for improved accuracy. The same procedure of imputation was employed for DNA polymorphisms on chromosome 14. On chromosome 14, 25,659 DNA putative DNA polymorphisms found in the parents were imputed onto the offspring, exploiting 2,359 DNA polymorphisms that were found in both sets of animals. Following imputation of DNA polymorphisms on chromosome 3 and 14, the imputed data sets were used in GWAS analysis, testing associations to both histopathology scores and cd8-qPCR, using the GWAS approach described above.

On chromosome 3 (GenBank identifier NC_027302.1), imputed DNA polymorphisms strongly correlated to histopathology scores were primarily found in the area stretching from position 78,364,536 bp to 91,273,924 bp (FIG. 3). The dbSNP identifiers, positions, and high-resistance/low-resistance alleles of the DNA polymorphisms on chromosome 3 most strongly associated to histopathology score are to be found in Table 3.

All DNA polymorphisms in Table 3 are capable of predicting resistance to heart and skeletal muscle infection. The DNA polymorphisms were identified in GWAS for histopathology score and/or cd8-qPCR, using imputed data. DNA polymorphisms associated to histopathology score and/or cd8-qPCR are not listed in Table 3 if they were already listed in Table 1.

On chromosome 14, imputed DNA polymorphisms strongly correlated to cd8-PCR values were primarily found in the area stretching from position 43,552,599 to 57,552,882 relative to the published chromosome sequence (GenBank identifier NC_027313.1). The dbSNP identifiers, positions, and high-resistance/low-resistance alleles of the DNA polymorphisms most strongly associated to cd8-qPCR scores are to be found in Table 4.

All DNA polymorphisms in Table 4 are capable of predicting resistance to heart and skeletal muscle infection. The DNA polymorphisms were identified in GWAS for cd8-qPCR, using imputed data. DNA polymorphisms associated to cd8-qPCR are not listed in Table 3 if they were already listed in Table 1.

In order to identify additional DNA polymorphisms associated to HSMI, the Inventors devised and implemented the following approach: 99 random Atlantic salmon originating from the same population as the parents and the offspring, were whole-genome sequenced on Illumina HighSeq 2000, producing paired-end reads to an average genome coverage of 18× (range 8× to 32×, assuming a genome size of 3.0 billion base pairs). The reads were aligned to the reference sequence of chromosome 3 or 14 of Atlantic salmon (GenBank identifiers NC_027302.1 or NC_027313.1).) using BWA mem version 0.7.10-r789 (Li and Durbin 2009). SNPs and short indels were identified using Freebayes version 0.9.15-1 (Garrison and Marth 2012); to filter away low-quality variants, using run-time parameters-use-mapping-quality and -min-mapping-quality 1, in addition to 'vcffilter-f "QUAL>20"'. The SNP-detection process also returned genotypes on the 99 animals, for all identified DNA polymorphisms. SNPs and short indels were annotated using snpEff version 4.0e (Cingolani et al. 2012). The snpEff annotation database was based on the CIGENE annotation version 2.0 (Lien et al., submitted). DNA polymorphisms in sufficiently strong LD ($r^2>0.5$) with the 'best' (most strongly associated to heart and skeletal muscle inflammation) DNA polymorphisms on chromosome 3 or chromosome 14 (more precisely, to DNA polymorphism ss1868447536 and/or ss1868368511 from chromosome 3 (Table 1) and DNA polymorphism ss1868307106 from chromosome 14 (Table 2)) were identified by running the computer program PLINK v1.9 (Chang et al. 2015) (options --r2 -Id-snp rs159406379 --chr-set 29 --no-xy --Id-window 999999999 --Id-window-kb 500). The list of such DNA polymorphisms was mapped against the annotation database, producing a list of DNA polymorphism that are 1) associated to resistance to heart and skeletal muscle inflammation and 2) putative functional according to the SnpEff annotation.

Table 5 contains a list of DNA polymorphisms derived using this LD-based approach. The table contains chromosome, positions and the identify of resistance- and non-resistance alleles of DNA polymorphisms, in addition to the names of the genes wherein the DNA polymorphisms reside and the annotated function of the DNA polymorphisms within these genes.

Table 6 contains the DNA sequences of all DNA polymorphisms listed in Tables 1, 2, 3, 4, and 5.

TABLE 1

DNA polymorphisms capable of predicting resistance to heart and skeletal muscle inflammation in Atlantic salmon. Ssid = identifier of the DNA polymorphism within the GenBank dbSNP database; chr/GenBank ID = chromosome number of the DNA polymorphism within the Atlantic salmon genome, and the GenBank ID of the chromosome sequence; pos = position of the DNA polymorphism within the GenBank sequence; res. allele and non-res. allele = identity of alleles conferring resistance and non-resistance to heart and skeletal muscle inflammation, respectively; p-value histopat. and p-value cd8-qPCR = p-value from tests for association between DNA polymorphisms and histopathology scores and cd8-qPCR values, respectively.

| DNA pol # | Ssid | Chr/GenBank ID | pos | res. allele | non-res. allele | p-value histopat. | p-value cd8-qPCR |
|---|---|---|---|---|---|---|---|
| 1 | ss1868447536 | 3/NC_027302.1 | 81438207 | A | G | 1.86E−13 | 7.38E−08 |
| 2 | ss1868822487 | 3/NC_027302.1 | 90860718 | A | C | 6.57E−12 | 4.99E−07 |
| 3 | ss1868354611 | 3/NC_027302.1 | 80185895 | G | A | 2.02E−10 | 9.25E−05 |
| 4 | ss1868795339 | 3/NC_027302.1 | 81446760 | A | G | 3.68E−09 | 0.00015859 |
| 5 | ss1868047992 | 3/NC_027302.1 | 70308540 | C | T | 4.03E−07 | 5.18E−05 |
| 6 | ss1868331125 | 3/NC_027302.1 | 80980820 | T | C | 7.45E−07 | 5.12E−05 |
| 7 | ss1868368511 | 3/NC_027302.1 | 90967849 | G | A | 0.00018551 | 2.34E−08 |
| 8 | ss1868396576 | 3/NC_027302.1 | 79186351 | A | G | 0.03444835 | 1.77E−07 |

TABLE 2

DNA polymorphisms capable of predicting resistance to heart and skeletal muscle inflammation in Atlantic salmon. Ssid = identifier of the DNA polymorphism within the GenBank dbSNP database; chr/GenBank ID = chromosome number of the DNA polymorphism within the Atlantic salmon genome, and the GenBank ID of the chromosome sequence; pos = position of the DNA polymorphism within the GenBank sequence; res. allele and non-res. allele = identity of alleles conferring resistance and non-resistance to heart and skeletal muscle inflammation, respectively; p-value cd8-qPCR = p-value from tests for association between DNA polymorphisms and cd8-qPCR values.

| DNA pol # | Ssid | Chr/GenBank ID | pos | res. allele | non-res. allele | p-value cd8-qPCR |
|---|---|---|---|---|---|---|
| 9 | ss1868307106 | 14/NC_027313.1 | 54098314 | G | A | 8.63E−08 |
| 10 | ss1868764075 | 14/NC_027313.1 | 53722865 | A | G | 1.41E−07 |
| 11 | ss1867927751 | 14/NC_027313.1 | 56768896 | A | G | 2.50E−07 |
| 12 | ss1868318796 | 14/NC_027313.1 | 53376433 | A | G | 7.58E−07 |

TABLE 3

DNA polymorphisms capable of predicting resistance to heart and skeletal muscle inflammation in Atlantic salmon. Ssid = identifier of the DNA polymorphism within the GenBank dbSNP database; chr/GenBank ID = chromosome number of the DNA polymorphism within the Atlantic salmon genome, and the GenBank ID of the chromosome sequence; pos = position of the DNA polymorphism within the GenBank sequence; res. allele and non-res. allele = identity of alleles conferring resistance and non-resistance to heart and skeletal muscle inflammation, respectively; p-value histopat. = p-value from tests for association between DNA polymorphisms and histopathology scores.

| DNA pol # | Ssid | Chr/GenBank ID | pos | res. allele | non-res. Allele | p-value histopat. |
|---|---|---|---|---|---|---|
| 13 | ss1868538659 | 3/NC_027302.1 | 89441560 | T | G | 6.75E−14 |
| 14 | ss1868161997 | 3/NC_027302.1 | 83185840 | T | C | 1.81E−13 |
| 15 | ss1868435260 | 3/NC_027302.1 | 91273924 | G | A | 2.05E−13 |
| 16 | ss1868124696 | 3/NC_027302.1 | 81717100 | G | A | 2.45E−13 |
| 17 | ss1868447536 | 3/NC_027302.1 | 81438207 | A | G | 2.73E−13 |
| 18 | ss1868365111 | 3/NC_027302.1 | 90342957 | T | G | 3.31E−13 |
| 19 | ss1868638847 | 3/NC_027302.1 | 81578538 | A | C | 4.49E−13 |
| 20 | ss1868822487 | 3/NC_027302.1 | 90860718 | A | C | 1.56E−12 |
| 21 | ss1868065680 | 3/NC_027302.1 | 83391479 | A | C | 3.51E−12 |
| 22 | ss1868469043 | 3/NC_027302.1 | 84674335 | G | A | 5.41E−12 |
| 23 | ss1868846411 | 3/NC_027302.1 | 81998536 | A | G | 5.53E−12 |
| 24 | ss1868822542 | 3/NC_027302.1 | 85851618 | G | A | 7.12E−12 |
| 25 | ss1868354611 | 3/NC_027302.1 | 80185895 | G | A | 1.25E−10 |
| 26 | ss1868256346 | 3/NC_027302.1 | 78364536 | C | T | 1.27E−10 |
| 27 | ss1868658490 | 3/NC_027302.1 | 89046115 | A | G | 2.41E−10 |
| 28 | ss1868596935 | 3/NC_027302.1 | 89147285 | C | T | 2.41E−10 |

TABLE 3-continued

DNA polymorphisms capable of predicting resistance to heart and skeletal muscle inflammation in Atlantic salmon. Ssid = identifier of the DNA polymorphism within the GenBank dbSNP database; chr/GenBank ID = chromosome number of the DNA polymorphism within the Atlantic salmon genome, and the GenBank ID of the chromosome sequence; pos = position of the DNA polymorphism within the GenBank sequence; res. allele and non-res. allele = identity of alleles conferring resistance and non-resistance to heart and skeletal muscle inflammation, respectively; p-value histopat. = p-value from tests for association between DNA polymorphisms and histopathology scores.

| DNA pol # | Ssid | Chr/GenBank ID | pos | res. allele | non-res. Allele | p-value histopat. |
|---|---|---|---|---|---|---|
| 29 | ss1868707552 | 3/NC_027302.1 | 88964614 | A | G | 3.84E−10 |
| 30 | ss1868609032 | 3/NC_027302.1 | 80186731 | A | G | 4.79E−10 |
| 31 | ss1868016481 | 3/NC_027302.1 | 81964975 | T | C | 7.39E−10 |
| 32 | ss1868225037 | 3/NC_027302.1 | 81446554 | A | G | 1.39E−09 |
| 33 | ss1868795339 | 3/NC_027302.1 | 81446760 | A | G | 1.43E−09 |
| 34 | ss1867950637 | 3/NC_027302.1 | 81434272 | C | T | 1.97E−09 |
| 35 | ss1868512714 | 3/NC_027302.1 | 81435622 | T | C | 1.97E−09 |
| 36 | ss1868391605 | 3/NC_027302.1 | 89376084 | T | C | 2.23E−09 |
| 37 | ss1868833692 | 3/NC_027302.1 | 84407555 | G | A | 5.30E−09 |
| 38 | ss1868833185 | 3/NC_027302.1 | 84235339 | T | C | 7.33E−09 |
| 39 | ss1867959638 | 3/NC_027302.1 | 84243207 | G | A | 7.33E−09 |
| 40 | ss1868803581 | 3/NC_027302.1 | 87252679 | A | G | 8.17E−09 |
| 41 | ss1868417386 | 3/NC_027302.1 | 59788304 | C | T | 8.44E−09 |
| 42 | ss1868147018 | 3/NC_027302.1 | 70020249 | G | A | 2.43E−06 |
| 43 | ss1868368511 | 3/NC_027302.1 | 91016402 | C | T | 1.22E−05 |

TABLE 4

DNA polymorphisms capable of predicting resistance to heart and skeletal muscle inflammation in Atlantic salmon. Ssid = identifier of the DNA polymorphism within the GenBank dbSNP database; chr/GenBank ID = chromosome number of the DNA polymorphism within the Atlantic salmon genome, and the GenBank ID of the chromosome sequence; pos = position of the DNA polymorphism within the GenBank sequence; res. allele and non-res. allele = identity of alleles conferring resistance and non-resistance to heart and skeletal muscle inflammation, respectively; p-value cd8-qPCR = p-value from tests for association between DNA polymorphisms and cd8-qPCR values.

| DNA pol # | Ssid | Chr/GenBank ID | pos | res. allele | non-res. allele | p-value cd8-qPCR |
|---|---|---|---|---|---|---|
| 44 | ss1868139598 | 14/NC_027313.1 | 51294667 | C | T | 2.84E−08 |
| 45 | ss1868332325 | 14/NC_027313.1 | 51406871 | G | A | 2.84E−08 |
| 46 | ss1868178221 | 14/NC_027313.1 | 43552599 | G | T | 3.93E−08 |
| 47 | ss1868319115 | 14/NC_027313.1 | 53447794 | G | A | 5.12E−08 |
| 48 | ss1868572240 | 14/NC_027313.1 | 53448484 | G | A | 5.12E−08 |
| 49 | ss1868640625 | 14/NC_027313.1 | 53322659 | C | A | 5.12E−08 |
| 50 | ss1868798676 | 14/NC_027313.1 | 53215491 | G | A | 7.25E−08 |
| 51 | ss1868380723 | 14/NC_027313.1 | 57552882 | C | G | 9.79E−08 |
| 52 | ss1868247261 | 14/NC_027313.1 | 45948549 | G | A | 9.79E−08 |
| 53 | ss1868437423 | 14/NC_027313.1 | 49052367 | G | A | 9.79E−08 |
| 54 | ss1868651852 | 14/NC_027313.1 | 52370012 | T | C | 9.79E−08 |
| 55 | ss1868188039 | 14/NC_027313.1 | 53279960 | G | T | 9.79E−08 |
| 56 | ss1868081927 | 14/NC_027313.1 | 53291831 | A | G | 9.79E−08 |
| 57 | ss1868083595 | 14/NC_027313.1 | 53299815 | G | T | 9.79E−08 |

TABLE 5

Functional DNA polymorphisms found be the Inventors to be associated to heart and skeletal muscle inflammation. The identifiers of the DNA polymorphisms are a combination of a short name for the Atlantic salmon chromosome wherein they reside (ssa03 = chromosome 3 or ssa14 = chromosome 14), followed by underscore and the position of the DNA polymorphism within the published sequence of the chromosomes (NC_027302.1 for chromosome 3 and NC_027313.1 for chromosome 14); res. allele and non-res. allele = identity of the alleles conferring resistance and non-resistance to heart and skeletal muscle inflammation, respectively.

| DNA pol # | identifier | Chr/GenBank ID | pos | res. allele | non-res. allele |
|---|---|---|---|---|---|
| 58 | ssa03_90078096 | 3/NC_027302.1 | 90078096 | G | T |
| 59 | ssa03_81619243 | 3/NC_027302.1 | 81619243 | C | T |
| 60 | ssa03_81620999 | 3/NC_027302.1 | 81620999 | G | A |
| 61 | ssa03_84674335 | 3/NC_027302.1 | 84674335 | G | A |
| 62 | ssa03_81618268 | 3/NC_027302,1 | 81618268 | G | A |
| 63 | ssa03_84675406 | 3/NC_027302.1 | 84675406 | T | A |

TABLE 6

Sequences of the DNA polymorphisms of the Invention. DNA sequences are oriented in the same direction (same DNA strand) as the published genome reference for Atlantic salmon (accession number GCA_000233375.4). The two alleles of each DNA polymorphism are given within brackets. The deletion allele of insertion-deletion DNA polymorphisms are annotated as '—'. SEQ ID res. allele = sequence number within the Sequence Listings File corresponding to the resistance allele of the DNA polymorphism in question; SEQ ID non-res. allele = sequence number within the Sequence Listings File corresponding to the non-resistance allele of the DNA polymorphism in question. All sequences are presented 5' to 3' relative to sequence GCA_000233375.4

| DNA POL # | SEQ ID RES. ALLELE | SEQ ID NON-RES. ALLELE | SEQUENCE |
|---|---|---|---|
| 1 | 1 | 64 | CCTATTGAGAAACCAGTTGGGTCATTGCTTACTGA[G/A]AAACCAGTAGGGACATTACCTATTGAGTAACCAGT |
| 2 | 2 | 65 | CAGAATGCCATCCTGAAGGATCTTGTGCTACAGTT[C/A]CTACTGAGAATAGTTTCCCGCCGCCTACTGGACAG |
| 3 | 3 | 66 | AGGTTAATGATTACCAGGTTAGCATGCGTGAGCAA[A/G]GCATTCACTACTCATGCGCTGGGAGAGCAGAAAAT |
| 4 | 4 | 67 | CCATCTATTTGATAGTCCTTTCCATATTTGATAGA[G/A]ACATATGCCCTAGGTGAATTTACACATTTTAAGCA |
| 5 | 5 | 68 | TTTTTCATTGCCATGCCAATTGATCTGAGTCTCCA[T/C]GTTGTCATTGCAGCAAGAGGTTGCACAGTACAGAA |
| 6 | 6 | 69 | GGTCACATGGCCTTTGAATAAACAGCAAAATACAT[C/T]CTCTCATGTACAAATCTTCCATCAGCCAAACGCTT |
| 7 | 7 | 70 | CACGGGGGGCCAGTACAAAAAAAATGCATGAAAT[G/A]AAATGGATGAAATGTATGAATTCACTACTGTAAGT |
| 8 | 8 | 71 | ACATGAAACGAGGGGTTAATATGATAATAAGAAGG[G/A]AGTTTTAATCTATAACACACCTCGTTTATTCTCCT |
| 9 | 9 | 72 | AAAACTATACATTTTGGTGGAAGGCAAAATCTTAA[G/A]CTCATTTGAGCTAAAACTCGCAAATATATTGGCTG |
| 10 | 10 | 73 | AAGCGGTTCGATGAGTCATTCTGGATCCAAGCCTT[A/G]TATGAGAAACTCACAGCTGCAACTCTAAGCCAAAC |
| 11 | 11 | 74 | CTGGACAGGCTCTTTGGTAGTGTTCGTGCTCTGTG[A/G]TGACTGTTCATCTTCAGCCTGGCTTGGCTGGTCTG |
| 12 | 12 | 75 | TTTATATCTCTTGGCGGTTATTAGTTACATTCTTT[G/A]TAAAATGAATAATAGAGCACAATATTCACTTGGCTA |
| 13 | 13 | 76 | TCAAACGACATGACGTAACAGGAACTACAGTAGAG[G/T]AATCTTGTCTCTGGCCTCTCAGAAATAGGTTAAGT |
| 14 | 14 | 77 | ATGGAAAATGCAGCCTCATCACAGTCCACTCCAGA[G/T]ACCTTCCCTAACGGCAGATTTCATGAGACATATCT |
| 15 | 15 | 78 | TAAATGCATGTGACCTACTACACCCTCCATTGACC[A/G]CTCCTGTAATTATATCCAGCCAGGTCAGTCCTTAG |
| 16 | 16 | 79 | TACACTAGCATATGAAACCACGTGACAAAGAATGA[A/G]AAGGTGCACTCTTTAGATCATCAACAAAAGAATGT |
| 17 | 17 | 80 | CCTATTGAGAAACCAGTTGGGTCATTGCTTACTGA[G/A]AAACCAGTAGGGACATTACCTATTGAGTAACCAGT |
| 18 | 18 | 81 | TGTTGACAGAGTCAGGTGCATGGCAGGTGACATAC[G/T]ATTGCTCCTTCAATGCCTATATCGTATGTGAGATA |
| 19 | 19 | 82 | CAAAAGCCACATCAACACAACATGAAGGCTAGATA[C/A]AGATATAGTGAAACAGAATCTTACAGTTTCCATGT |
| 20 | 20 | 83 | CAGAATGCCATCCTGAAGGATCTTGTGCTACAGTT[C/A]CTACTGAGAATAGTTTCCCGCCGCCTACTGGACAG |
| 21 | 21 | 84 | TCTGTTGATGTCTATATTTGGCTAATATTCTTTTT[C/A]ATTTTCTGTTTCAGAGTGGGCAGTTTGACTATGAC |
| 22 | 22 | 85 | AGCTAGAGTTGTTGGTGACAGTAAAGGAGAAAGAG[A/G]GGACCGGCCAGCCATGTGTCAGCAATTGAGAAATG |
| 23 | 23 | 86 | AATATGCGTGTCACAGTTCCCATTTCTGAGGCTGA[G/A]AGATAAACAGGCAGAGATAAACAGTCACAATGGTT |
| 24 | 24 | 87 | TCCCAGGTGGCACTGATAGATGAGTACACATTCCC[A/G]GTAGGATCAATGTTTGTTCGCACCCTGCTATTCTT |
| 25 | 25 | 88 | AGGTTAATGATTACCAGGTTAGCATGCGTGAGCAA[A/G]GCATTCACTACTCATGCGCTGGGAGAGCAGAAAAT |
| 26 | 26 | 89 | GCGCTCGCCATAGTCTCCTCATTGTGTAACTATAA[T/C]CATGGAGAAATATGTGCAACAACACAGTTGAGACT |
| 27 | 27 | 90 | CCCGTCTGTCAGTCATTCCATGTTCGGTGTCATTA[G/A]CTGAGGGCTGAAGCACGGACGTTGAACAGAAGCTC |
| 28 | 28 | 91 | TAAAATGGCAGTTAAGTCAGCTTGTATATTGGGTC[T/C]AAAGATAACAGTTAATGTGCTGAGGCTTGATAAAC |
| 29 | 29 | 92 | ACTCTGCCCAAACACACACTCTCTGTCTCTGCCAG[G/A]TGATCCAGCCCCCTGCTCACGCTACATCTTCTCGC |
| 30 | 30 | 93 | TAATCTACAGCCAATGCAAGTACATTCTGTCGACC[G/A]AAGAGCTCTGGCCATATCAGCCCTGTTATGACCAT |
| 31 | 31 | 94 | TACACGGTACACTTGCTGCACTATATAAAAACACT[C/T]GGGTCCACAGCGGGAGAAGAAAGTCACGGCTTTAA |
| 32 | 32 | 95 | CCAGTTGGGACATTTCCTATTGAGAAACCAGTCGG[G/A]ATATTACCTGTTGAGAAACCAGTTGGGACATTACC |
| 33 | 33 | 96 | CCATCTATTTGATAGTCCTTTCCATATTTGATAGA[G/A]ACATATGCCCTAGGTGAATTTACACATTTTAAGCA |
| 34 | 34 | 97 | TCGGGACGTTGCCTATTGAGAAACTAATTGGGATA[T/C]TGCCTATTGAGAAGCAAGTTGGGACATTGCCCATT |
| 35 | 35 | 98 | TTGAGAAACAAGTTGGGATATTGCCCGTTGAGATG[C/T]TAGTTGGGACATTGCCCATTGAGAAACCAGTCGGG |
| 36 | 36 | 99 | TGAGCGTAGTATGACAGAGTGGTAGTTAGTTGTCT[C/T]ACTGACCCTCCGTAGCTGGTTGGTGAAGAACAGGG |
| 37 | 37 | 100 | CTAGTTCCCACTTCACAGGAGGGACATTTAAAAAT[A/G]CATGCAAGTGATATGTAAATATGAGTAAAAGGGTT |
| 38 | 38 | 101 | CAGTACATACAAAACTGTAGCCAAGAATGCATTTC[C/T]GTAAGCTTGAATTACTATCATATCAGTCTTTACAG |
| 39 | 39 | 102 | TTCAACAGATGCCTTTAGCCCAAGCTGATGAAACG[A/G]ATACAGATGCCATCATTGGGGCAGATTAAACATGT |
| 40 | 40 | 103 | TCAGTTTTCTCAAGTGTCTGTCTGACCGTGTCGTT[G/A]TCAAACCAGTTCCAGATCGCAGGCCTTGGAAGCCG |
| 41 | 41 | 104 | CAACAGCCTAGCCCAAGGCTGTCCAACCCCGTTCC[T/C]GGAGAGCTAACATCAGCCCGCTGCCTGGCTAGTGT |
| 42 | 42 | 105 | CCTCCCCCAATGCCAAATGCCTCATATCTGTTGGA[A/G]CCTCCACAGAGAATGGCATCTGAAAACATGTTTA |
| 43 | 43 | 106 | GCAGCACTGATGAAGGCATTGAAGCCTTTTGTTAA[C/T]ATTTTGAGCATGGGTTTAATTAAGTACATTTTTGC |
| 44 | 44 | 107 | TCCTCTTCAAATTGGACACAAGTCTTCGTCCTCAT[C/T]TCTCTCTGCATCTTCATTTTCCTCCTTCTCTGAAT |

TABLE 6-continued

Sequences of the DNA polymorphisms of the Invention. DNA sequences are oriented in the same direction (same DNA strand) as the published genome reference for Atlantic salmon (accession number GCA_000233375.4). The two alleles of each DNA polymorphism are given within brackets. The deletion allele of insertion-deletion DNA polymorphisms are annotated as '—'. SEQ ID res. allele = sequence number within the Sequence Listings File corresponding to the resistance allele of the DNA polymorphism in question; SEQ ID non-res. allele = sequence number within the Sequence Listings File corresponding to the non-resistance allele of the DNA polymorphism in question. All sequences are presented 5' to 3' relative to sequence GCA_000233375.4

| DNA POL # | SEQ ID RES. ALLELE | SEQ ID NON-RES. ALLELE | SEQUENCE |
|---|---|---|---|
| 45 | 45 | 108 | GGTTGTTTCCCAAACATAAATTGATATGGAGAGTC[G/A]TGTCATTTCGTGTCATTTCTTGTGCAATTATATGC |
| 46 | 46 | 109 | ATGGCAGCAAGTAGGGTGGACGAAATGGAGGACAT[T/G]GAGAAAAAGCTGGTGAAGCAGCAGCTGTGCTGGAA |
| 47 | 47 | 110 | CAAACATCAAATATCCGTGCTAAATGAAATGGCAA[G/A]CTAACATAAATTAGCTTGATCGTTTAATAAGTACT |
| 48 | 48 | 111 | AGGCACCATAAGACTCCAAGAGGACACTAACAGCT[G/A]GTGAAAAACATGGACCTGGGTCCTGTTATCCTTGT |
| 49 | 49 | 112 | GGTTCGGGGGAGCTGTGTTACCGTGCACTGTCTAT[C/A]TCAGATTGCTAAATAATTACCATGACTGCTTCTGA |
| 50 | 50 | 113 | AACAGCAGTGCCAGAGAAGGAACTTTACATTTAAT[G/A]TAATTCTGAGTCATTAACATTTGGCTGGACGGTGT |
| 51 | 51 | 114 | AGGGTATAGATGGGCTCATGACCATGACCTCCACC[C/G]TTACCTTTACCGCCTCCCTCCGCCATCACGGGCTG |
| 52 | 52 | 115 | TGAAAAGGCGTAGGGAGAGAGAAGCGAAGAGACAGA[G/A]AAAATACGCTAATATCAGGTGTTGTTCTGAGTTTC |
| 53 | 53 | 116 | CAACAGGAGATAAACCCCTCTACTGTGCAGCAGGG[G/A]AGAACAGATATTCACAATCAGGGCTGCAATACAGA |
| 54 | 54 | 117 | CTGTCTGTCCACTAAATCACTGGATATATATATGA[C/T]GGGCTGACGGGACAGGACAGGGAGACATATGAGGG |
| 55 | 55 | 118 | TTCCATGATGTAACTTAAGATGCCCCACTGTGTAG[G/T]TGGAAAGAGTGATGAGATGTGGGCAAGAAAAGTAG |
| 56 | 56 | 119 | TAAAATCATGGGGACGGTCTCTGAGAAAATGCACT[A/G]AACAAACCAATACTATTTTTTTTTCATATTGCAA |
| 57 | 57 | 120 | ACTAGAAATTATGCAAGCAGATTGACTTAATACCA[G/T]TCTGGCCTATAGGGTTGTTTTTTTATTCAGACATG |
| 58 | 58 | 121 | AGCCTCCAGGTTGGTCTCAGGGTTTAAGACCTACC[T/G]TTCATTCTGAATAGCCTCCAGGTTGGCACGGCTGT |
| 59 | 59 | 122 | GCTGGCCTGCTTCTCCTCGTCCTCATCTGGCTGTG[T/C]GCAGCGGAGTGTGTAAGTAGCCTAATCCACCTGAA |
| 60 | 60 | 123 | AGCCAAGAAAAAAACTGCAATTTTATTAATAGTTT[A/G]AAAGAAGCTCCATAGTTCATGAAAACATTGTTTTC |
| 61 | 61 | 124 | AGCTAGAGTTGTTGGTGACAGTAAAGGAGAAAGAG[A/G]GGACCGGCCAGCCATGTGTCAGCAATTGAGAAATG |
| 62 | 62 | 125 | CGGCTGTACAAAGATCGTCTGAAGGTCACAGGCGG[A/G]TTGAACTCTGACCTGCTCAACGTGACCATAGCCCA |
| 63 | 63 | 126 | GCACTTGTTAGCCTAGCCTAGTTTAGCCTAGCCTC[A/T]GAGATAGATGCTTGTGGATTTCCCTCAGGCAGAAT |

REFERENCES

Biering, E. and Garseth, Å. H. (2012). Heart and skeletal muscle inflammation (HSMI) of farmed Atlantic salmon (*Salmo salar* L.) and the associated Piscine reovirus (PRV). ICES Identification Leaflets for Diseases and Parasites of Fish and Shellfish. Leaflet No. 58. 6 pp.

Chang C C, Chow C C, Tellier LCAM, Vattikuti S, Purcell S M and Lee J J (2015) Second-generation PLINK: rising to the challenge of larger and richer datasets. Gigascience 4: 7.

Cingolani P, Platts A, Wang le L, Coon M, Nguyen T, Wang L, Land S J, Xu L, and Ruden D M (2012) A program for annotating and predicting the effects of single nucleotide polymorphisms, SnpEff: SNPs in the genome of *Drosophila melanogaster* strain w118; iso-2; iso-3. Fly 6: 80-92.

Garrison E and Marth G (2012) Haplotype-based variant detection from short-read sequencing. arXiv: 1207.3907v2 [q-bio.GN] 20 Jul. 2012.

Gjedrem T, Gjøen H M, and Gjerde B (1991) Genetic origin of Norwegian Farmed salmon. Aquaculture 98: 41-50.

Godoy M G, Kibenge M J T, Wang Y, Suarez R, Leiva C, Vallejos F, and Kibenge F S B (2016). First description of clinical presentation of piscine orthoreovirus (PRV) infections in salmonid aquaculture in Chile and identification of a second genotype (Genotype II) of PRV. Virology Journal 13:98.

Hjeltnes B, Walde C, Bang Jensen B, Haukaas A (ed.) (2016). The Fish Health Report 2015. The Norwegian Veterinary Institute 2016.

Hjeltnes B, Walde C, Bang jensen B, Haukaas A (red) (2016). The Fish Health Report 2015. The Norwegian Veterinary Institute 2016.

Kongtorp R T, Kjerstad A, Taksdal T, Guttvik A, and Falk K (2004) Heart and skeletal muscle inflammation in Atlantic salmon, *Salmo salar* L.: a new infectious disease. J Fish Dis. 2004, 27: 351-358.

Li H and Durbin R (2009) Fast and accurate short read alignment with Burrows-Wheeler transform. Bioinformatics 25: 1754-60.

Olsen A B, Hjortaas M, Tengs T, Hellberg H, and Johansen R (2015) First Description of a New Disease in Rainbow Trout (*Oncorhynchus mykiss* (Walbaum)) Similar to Heart and Skeletal Muscle Inflammation (HSMI) and Detection of a Gene Sequence Related to Piscine Orthoreovirus (PRV). PLoS ONE 10: e0131638.

Palacios G, Løvoll M, Tengs T, Hornig M, Hutchison S, Hui J, Kongtorp R T, Savji N, Bussetti A V, Solovyov A, Kristoffersen A B, Celone C, Street C, Trifonov V, Hirschberg D L, Rabadan R, Egholm M, Rimstad E, Lipkin W I (2010) Heart and skeletal muscle inflammation of farmed salmon is associated with infection with a novel reovirus. PLoS One 5: e11487-10.

The invention claimed is:

1. A method of detecting one or more salmonid gene variants:
   a) obtaining a sample from a salmonid;
   b) assaying the sample to detect one or more salmonid gene variants; and
   c) detecting the presence of an adenine at position 36 of SEQ. ID NO. 2.

2. The method of claim 1, wherein detecting the presence of an adenine at position 36 of SEQ. ID NO. 2 comprises sequence analysis of the sample.

3. The method of claim 1, wherein the method further comprises detecting the presence of a guanine residue at position 36 of SEQ ID NO. 1, 7 or 9.

4. The method of claim 1, wherein the method further comprises detecting the presence of a guanine residue at position 36 of SEQ ID NO. 1, 7 9, or 13, a cytosine residue at position 36 of SEQ ID NO. 14, an adenine residue at position 36 of SEQ ID NO. 15, or SEQ ID NO. 16.

5. The method of claim 1, wherein the salmonid is an Atlantic salmon (i.e. *Salmo salar*), rainbow trout (i.e. *Oncorhynchus mykiss*), or coho salmon (i.e. *Oncorhynchus kisutch*).

6. The method of claim 1, further comprising breeding from the salmonid, based on the detected allele of an adenine at position 36 of SEQ ID NO. 2.

7. A method of producing salmonid offspring, the method comprising:
   producing offspring from a salmonid wherein the salmonid has an adenine at position 36 of SEQ ID NO. 2, wherein a sample from the salmonid has been tested to detect the presence of an adenine at position 36 of SEQ ID NO. 2.

8. The method of claim 7, wherein the offspring comprises eggs for fertilization.

9. The method of claim 7, wherein producing offspring comprises fertilizing eggs from the salmonid.

10. A method of breeding salmonid, the method comprising:
    breeding from a salmonid wherein the salmonid has an adenine at position 36 of SEQ ID NO. 2, wherein a sample from the salmonid has been tested to detect the presence of an adenine at position 36 of SEQ ID NO. 2.

* * * * *

SEQUENCE LISTING

<160> NUMBER OF SEQ ID NOS: 132

<210> SEQ ID NO 1
<211> LENGTH: 71
<212> TYPE: DNA
<213> ORGANISM: Atlantic salmon

```
<400> SEQUENCE: 1
cctattgaga aaccagttgg gtcattgctt actgaaaaac cagtagggac attacctatt    60
gagtaaccag t                                                         71

<210> SEQ ID NO 2
<211> LENGTH: 71
<212> TYPE: DNA
<213> ORGANISM: Atlantic salmon

<400> SEQUENCE: 2
cagaatgcca tcctgaagga tcttgtgcta cagttactac tgagaatagt ttcccgccgc    60
ctactggaca g                                                         71

<210> SEQ ID NO 3
<211> LENGTH: 71
<212> TYPE: DNA
<213> ORGANISM: Atlantic salmon

<400> SEQUENCE: 3
aggttaatga ttaccaggtt agcatgcgtg agcaaggcat tcactactca tgcgctggga    60
gagcagaaaa t                                                         71

<210> SEQ ID NO 4
<211> LENGTH: 71
<212> TYPE: DNA
<213> ORGANISM: Atlantic salmon

<400> SEQUENCE: 4
ccatctattt gatagtcctt tccatatttg atagaaacat atgccctagg tgaatttaca    60
cattttaagc a                                                         71

<210> SEQ ID NO 5
<211> LENGTH: 71
<212> TYPE: DNA
<213> ORGANISM: Atlantic salmon

<400> SEQUENCE: 5
tttttcattg ccatgccaat tgatctgagt ctccacgttg tcattgcagc aagaggttgc    60
acagtacaga a                                                         71

<210> SEQ ID NO 6
<211> LENGTH: 71
<212> TYPE: DNA
<213> ORGANISM: Atlantic salmon

<400> SEQUENCE: 6
ggtcacatgg cctttgaata aacagcaaaa tacattctct catgtacaaa tcttccatca    60
gccaaacgct t                                                         71

<210> SEQ ID NO 7
<211> LENGTH: 71
<212> TYPE: DNA
<213> ORGANISM: Atlantic salmon

<400> SEQUENCE: 7 cacgggggc cagtacaaaa aaaaatgcat gaaatgaaat ggatgaaatg tatgaattca    60
ctactgtaag t                                                         71
```

```
<210> SEQ ID NO 8
<211> LENGTH: 71
<212> TYPE: DNA
<213> ORGANISM: Atlantic salmon

<400> SEQUENCE: 8
acatgaaacg aggggttaat atgataataa gaaggaagtt ttaatctata acacacctcg    60
tttattctcc t                                                         71

<210> SEQ ID NO 9
<211> LENGTH: 71
<212> TYPE: DNA
<213> ORGANISM: Atlantic salmon

<400> SEQUENCE: 9
aaaactatac attttggtgg aaggcaaaat cttaagctca tttgagctaa aactcgcaaa    60
tatattggct g                                                         71

<210> SEQ ID NO 10
<211> LENGTH: 71
<212> TYPE: DNA
<213> ORGANISM: Atlantic salmon

<400> SEQUENCE: 10
aagcggttcg atgagtcatt ctggatccaa gccttatatg agaaactcac agctgcaact    60
ctaagccaaa c                                                         71

<210> SEQ ID NO 11
<211> LENGTH: 71
<212> TYPE: DNA
<213> ORGANISM: Atlantic salmon

<400> SEQUENCE: 11
ctggacaggc tctttggtag tgttcgtgct ctgtgatgac tgttcatctt cagcctggct    60
tggctggtct g                                                         71

<210> SEQ ID NO 12
<211> LENGTH: 71
<212> TYPE: DNA
<213> ORGANISM: Atlantic salmon

<400> SEQUENCE: 12
tttatatctc ttggcggtta ttagttacat tctttataaa atgataatag agcacaatat    60
tcacttggct a                                                         71

<210> SEQ ID NO 13
<211> LENGTH: 71
<212> TYPE: DNA
<213> ORGANISM: Atlantic salmon

<400> SEQUENCE: 13
tcaaacgaca tgacgtaaca ggaactacag tagagtaatc ttgtctctgg cctctcagaa    60
ataggttaag t                                                         71

<210> SEQ ID NO 14
<211> LENGTH: 71
<212> TYPE: DNA
<213> ORGANISM: Atlantic salmon

<400> SEQUENCE: 14
```

```
atggaaaatg cagcctcatc acagtccact ccagatacct tccctaacgg cagatttcat    60
gagacatatc t                                                         71

<210> SEQ ID NO 15
<211> LENGTH: 71
<212> TYPE: DNA
<213> ORGANISM: Atlantic salmon

<400> SEQUENCE: 15
taaatgcatg tgacctacta caccctccat tgaccgctcc tgtaattata tccagccagg    60
tcagtcctta g                                                         71

<210> SEQ ID NO 16
<211> LENGTH: 71
<212> TYPE: DNA
<213> ORGANISM: Atlantic salmon

<400> SEQUENCE: 16
tacactagca tatgaaacca cgtgacaaag aatgagaagg tgcactcttt agatcatcaa    60
caaaaagatg t                                                         71

<210> SEQ ID NO 17
<211> LENGTH: 71
<212> TYPE: DNA
<213> ORGANISM: Atlantic salmon

<400> SEQUENCE: 17
cctattgaga aaccagttgg gtcattgctt actgaaaaac cagtagggac attacctatt    60
gagtaaccag t                                                         71

<210> SEQ ID NO 18
<211> LENGTH: 71
<212> TYPE: DNA
<213> ORGANISM: Atlantic salmon

<400> SEQUENCE: 18
tgttgacaga gtcaggtgca tggcaggtga catactattg ctccttcaat gcctatatcg    60
tatgtgagat a                                                         71

<210> SEQ ID NO 19
<211> LENGTH: 71
<212> TYPE: DNA
<213> ORGANISM: Atlantic salmon

<400> SEQUENCE: 19
caaaagccac atcaacacaa catgaaggct agataaagat atagtgaaac agaatcttac    60
agtttccatg t                                                         71

<210> SEQ ID NO 20
<211> LENGTH: 71
<212> TYPE: DNA
<213> ORGANISM: Atlantic salmon

<400> SEQUENCE: 20
cagaatgcca tcctgaagga tcttgtgcta cagttactac tgagaatagt ttcccgccgc    60
ctactggaca g                                                         71

<210> SEQ ID NO 21
<211> LENGTH: 71
```

```
<210> SEQ ID NO 21
<211> LENGTH: 71
<212> TYPE: DNA
<213> ORGANISM: Atlantic salmon

<400> SEQUENCE: 21
tctgttgatg tctatatttg gctaatattc tttttaattt tctgtttcag agtgggcagt      60
ttgactatga c                                                         71

<210> SEQ ID NO 22
<211> LENGTH: 71
<212> TYPE: DNA
<213> ORGANISM: Atlantic salmon

<400> SEQUENCE: 22
agctagagtt gttggtgaca gtaaaggaga aagaggggac cggccagcca tgtgtcagca      60
attgagaaat g                                                         71

<210> SEQ ID NO 23
<211> LENGTH: 71
<212> TYPE: DNA
<213> ORGANISM: Atlantic salmon

<400> SEQUENCE: 23
aatatgcgtg tcacagttcc catttctgag gctgaaagat aaacaggcag agataaacag      60
tcacaatggt t                                                         71

<210> SEQ ID NO 24
<211> LENGTH: 71
<212> TYPE: DNA
<213> ORGANISM: Atlantic salmon

<400> SEQUENCE: 24
tcccaggtgg cactgataga tgagtacaca ttcccggtag gatcaatgtt tgttcgcacc      60
ctgctattct t                                                         71

<210> SEQ ID NO 25
<211> LENGTH: 71
<212> TYPE: DNA
<213> ORGANISM: Atlantic salmon

<400> SEQUENCE: 25
aggttaatga ttaccaggtt agcatgcgtg agcaaggcat tcactactca tgcgctggga      60
gagcagaaaa t                                                         71

<210> SEQ ID NO 26
<211> LENGTH: 71
<212> TYPE: DNA
<213> ORGANISM: Atlantic salmon

<400> SEQUENCE: 26
gcgctcgcca tagtctcctc attgtgtaac tataaccatg gagaaatatg tgcaacaaca      60
cagttgagac t                                                         71

<210> SEQ ID NO 27
<211> LENGTH: 71
<212> TYPE: DNA
<213> ORGANISM: Atlantic salmon

<400> SEQUENCE: 27
cccgtctgtc agtcattcca tgttcggtgt cattaactga gggctgaagc acggacgttg      60
```
aacagaagct c                                                          71

<210> SEQ ID NO 28
<211> LENGTH: 71
<212> TYPE: DNA
<213> ORGANISM: Atlantic salmon

<400> SEQUENCE: 28
taaaatggca gttaagtcag cttgtatatt gggtccaaag ataacagtta atgtgctgag    60
gcttgataaa c                                                          71

<210> SEQ ID NO 29
<211> LENGTH: 71
<212> TYPE: DNA
<213> ORGANISM: Atlantic salmon

<400> SEQUENCE: 29
actctgccca aacacacact ctctgtctct gccagatgat ccagcccct gctcacgcta     60 catcttctcg c                                                          71

<210> SEQ ID NO 30
<211> LENGTH: 71
<212> TYPE: DNA
<213> ORGANISM: Atlantic salmon

<400> SEQUENCE: 30
taatctacag ccaatgcaag tacattctgt cgaccaaaga gctctggcca tatcagccct    60
gttatgacca t                                                          71

<210> SEQ ID NO 31
<211> LENGTH: 71
<212> TYPE: DNA
<213> ORGANISM: Atlantic salmon

<400> SEQUENCE: 31
tacacggtac acttgctgca ctatataaaa acacttgggt ccacagcggg agaagaaagt    60
cacggcttta a                                                          71

<210> SEQ ID NO 32
<211> LENGTH: 71
<212> TYPE: DNA
<213> ORGANISM: Atlantic salmon

<400> SEQUENCE: 32
ccagttggga catttcctat tgagaaacca gtcggaatat tacctgttga gaaaccagtt    60
gggacattac c                                                          71

<210> SEQ ID NO 33
<211> LENGTH: 71
<212> TYPE: DNA
<213> ORGANISM: Atlantic salmon

<400> SEQUENCE: 33
ccatctattt gatagtcctt tccatatttg atagaaacat atgccctagg tgaatttaca    60
cattttaagc a                                                          71

<210> SEQ ID NO 34
<211> LENGTH: 71
<212> TYPE: DNA
<213> ORGANISM: Atlantic salmon

```
<400> SEQUENCE: 34
tcgggacgtt gcctattgag aaactaattg ggatactgcc tattgagaag caagttggga    60
cattgcccat t                                                         71

<210> SEQ ID NO 35
<211> LENGTH: 71
<212> TYPE: DNA
<213> ORGANISM: Atlantic salmon

<400> SEQUENCE: 35
ttgagaaaca agttgggata ttgcccgttg agatgttagt tgggacattg cccattgaga    60
aaccagtcgg g                                                         71

<210> SEQ ID NO 36
<211> LENGTH: 71
<212> TYPE: DNA
<213> ORGANISM: Atlantic salmon

<400> SEQUENCE: 36
tgagcgtagt atgacagagt ggtagttagt tgtcttactg accctccgta gctggttggt    60
gaagaacagg g                                                         71

<210> SEQ ID NO 37
<211> LENGTH: 71
<212> TYPE: DNA
<213> ORGANISM: Atlantic salmon

<400> SEQUENCE: 37
ctagttccca cttcacagga gggacattta aaaatgcatg caagtgatat gtaaatatga    60
gtaaaagggt t                                                         71

<210> SEQ ID NO 38
<211> LENGTH: 71
<212> TYPE: DNA
<213> ORGANISM: Atlantic salmon

<400> SEQUENCE: 38
cagtacatac aaaactgtag ccaagaatgc atttctgtaa gcttgaatta ctatcatatc    60
agtctttaca g                                                         71

<210> SEQ ID NO 39
<211> LENGTH: 71
<212> TYPE: DNA
<213> ORGANISM: Atlantic salmon

<400> SEQUENCE: 39
ttcaacagat gcctttagcc caagctgatg aaacggatac agatgccatc attggggcag    60
attaaacatg t                                                         71

<210> SEQ ID NO 40
<211> LENGTH: 71
<212> TYPE: DNA
<213> ORGANISM: Atlantic salmon

<400> SEQUENCE: 40
tcagttttct caagtgtctg tctgaccgtg tcgttatcaa accagttcca gatcgcaggc    60
cttggaagcc g                                                         71
```

<210> SEQ ID NO 41
<211> LENGTH: 71
<212> TYPE: DNA
<213> ORGANISM: Atlantic salmon

<400> SEQUENCE: 41
caacagccta gcccaaggct gtccaacccc gttcccggag agctaacatc agcccgctgc    60
ctggctagtg t    71

<210> SEQ ID NO 42
<211> LENGTH: 71
<212> TYPE: DNA
<213> ORGANISM: Atlantic salmon

<400> SEQUENCE: 42
cctcccccaa tgccaaatgc tcatatctg ttggagcctc acagagaat ggcatctgaa    60 aaacatgttt a    71

<210> SEQ ID NO 43
<211> LENGTH: 71
<212> TYPE: DNA
<213> ORGANISM: Atlantic salmon

<400> SEQUENCE: 43
gcagcactga tgaaggcatt gaagcctttt gttaacattt tgagcatggg tttaattaag    60
tacatttttg c    71

<210> SEQ ID NO 44
<211> LENGTH: 71
<212> TYPE: DNA
<213> ORGANISM: Atlantic salmon

<400> SEQUENCE: 44
tcctcttcaa attggacaca agtcttcgtc ctcatctctc tctgcatctt cattttcctc    60
cttctctgaa t    71

<210> SEQ ID NO 45
<211> LENGTH: 71
<212> TYPE: DNA
<213> ORGANISM: Atlantic salmon

<400> SEQUENCE: 45
ggttgtttcc caaacataaa ttgatatgga gagtcgtgtc atttcgtgtc atttcttgtg    60
caattatatg c    71

<210> SEQ ID NO 46
<211> LENGTH: 71
<212> TYPE: DNA
<213> ORGANISM: Atlantic salmon

<400> SEQUENCE: 46
atggcagcaa gtagggtgga cgaaatggag gacatggaga aaaagctggt gaagcagcag    60
ctgtgctgga a    71

<210> SEQ ID NO 47
<211> LENGTH: 71
<212> TYPE: DNA
<213> ORGANISM: Atlantic salmon

<400> SEQUENCE: 47

```
caaacatcaa atatccgtgc taaatgaaat ggcaagctaa cataaattag cttgatcgtt    60
taataagtac t                                                        71

<210> SEQ ID NO 48
<211> LENGTH: 71
<212> TYPE: DNA
<213> ORGANISM: Atlantic salmon

<400> SEQUENCE: 48
aggcaccata agactccaag aggacactaa cagctggtga aaaacatgga cctgggtcct    60
gttatccttg t                                                        71

<210> SEQ ID NO 49
<211> LENGTH: 71
<212> TYPE: DNA
<213> ORGANISM: Atlantic salmon

<400> SEQUENCE: 49
ggttcggggg agctgtgtta ccgtgcactg tctatctcag attgctaaat aattaccatg    60
actgcttctg a                                                        71

<210> SEQ ID NO 50
<211> LENGTH: 71
<212> TYPE: DNA
<213> ORGANISM: Atlantic salmon

<400> SEQUENCE: 50
aacagcagtg ccagagaagg aactttacat ttaatgtaat tctgagtcat taacatttgg    60
ctggacggtg t                                                        71

<210> SEQ ID NO 51
<211> LENGTH: 71
<212> TYPE: DNA
<213> ORGANISM: Atlantic salmon

<400> SEQUENCE: 51
agggtataga tgggctcatg accatgacct ccaccttac ctttaccgcc tccctccgcc     60
atcacgggct g                                                        71

<210> SEQ ID NO 52
<211> LENGTH: 71
<212> TYPE: DNA
<213> ORGANISM: Atlantic salmon

<400> SEQUENCE: 52
tgaaaaggcg taggagagag aagcgaagag acagagaaaa tacgctaata tcaggtgttg    60
ttctgagttt c                                                        71

<210> SEQ ID NO 53
<211> LENGTH: 71
<212> TYPE: DNA
<213> ORGANISM: Atlantic salmon

<400> SEQUENCE: 53
caacaggaga taaacccctc tactgtgcag caggggagaa cagatattca caatcagggc    60
tgcaatacag a                                                        71

<210> SEQ ID NO 54
```

```
<211> LENGTH: 71
<212> TYPE: DNA
<213> ORGANISM: Atlantic salmon

<400> SEQUENCE: 54
ctgtctgtcc actaaatcac tggatatata tatgatgggc tgacgggaca ggacagggag      60
acatatgagg g                                                          71

<210> SEQ ID NO 55
<211> LENGTH: 71
<212> TYPE: DNA
<213> ORGANISM: Atlantic salmon

<400> SEQUENCE: 55
ttccatgatg taacttaaga tgccccactg tgtaggtgga agagtgatg agatgtgggc       60 aagaaaagta g                                                          71

<210> SEQ ID NO 56
<211> LENGTH: 71
<212> TYPE: DNA
<213> ORGANISM: Atlantic salmon

<400> SEQUENCE: 56
taaaatcatg gggacggtct ctgagaaaat gcactaaaca aaccaatact attttttttt      60
tcatattgca a                                                          71

<210> SEQ ID NO 57
<211> LENGTH: 71
<212> TYPE: DNA
<213> ORGANISM: Atlantic salmon

<400> SEQUENCE: 57
actagaaatt atgcaagcag attgacttaa taccagtctg gcctataggg ttgttttttt      60
attcagacat g                                                          71

<210> SEQ ID NO 58
<211> LENGTH: 71
<212> TYPE: DNA
<213> ORGANISM: Atlantic salmon

<400> SEQUENCE: 58
agcctccagg ttggtctcag ggtttaagac ctaccgttca ttctgaatag cctccaggtt      60
ggcacggctg t                                                          71

<210> SEQ ID NO 59
<211> LENGTH: 71
<212> TYPE: DNA
<213> ORGANISM: Atlantic salmon

<400> SEQUENCE: 59
gctggcctgc ttctcctcgt cctcatctgg ctgtgcgcag cggagtgtgt aagtagccta      60
atccacctga a                                                          71

<210> SEQ ID NO 60
<211> LENGTH: 71
<212> TYPE: DNA
<213> ORGANISM: Atlantic salmon

<400> SEQUENCE: 60
agccaagaaa aaaactgcaa ttttattaat agtttgaaag aagctccata gttcatgaaa      60
``` acattgttttc 71

<210> SEQ ID NO 61
<211> LENGTH: 71
<212> TYPE: DNA
<213> ORGANISM: Atlantic salmon

<400> SEQUENCE: 61
agctagagtt gttggtgaca gtaaaggaga aagaggggac cggccagcca tgtgtcagca  60
attgagaaat g  71

<210> SEQ ID NO 62
<211> LENGTH: 71
<212> TYPE: DNA
<213> ORGANISM: Atlantic salmon

<400> SEQUENCE: 62
cggctgtaca aagatcgtct gaaggtcaca ggcgggttga actctgacct gctcaacgtg  60
accatagccc a  71

<210> SEQ ID NO 63
<211> LENGTH: 71
<212> TYPE: DNA
<213> ORGANISM: Atlantic salmon

<400> SEQUENCE: 63
gcacttgtta gcctagccta gtttagccta gcctctgaga tagatgcttg tggatttccc  60
tcaggcagaa t  71

<210> SEQ ID NO 64
<211> LENGTH: 71
<212> TYPE: DNA
<213> ORGANISM: Atlantic salmon

<400> SEQUENCE: 64
cctattgaga aaccagttgg gtcattgctt actgagaaac cagtagggac attacctatt  60
gagtaaccag t  71

<210> SEQ ID NO 65
<211> LENGTH: 71
<212> TYPE: DNA
<213> ORGANISM: Atlantic salmon

<400> SEQUENCE: 65
cagaatgcca tcctgaagga tcttgtgcta cagttcctac tgagaatagt ttcccgccgc  60
ctactggaca g  71

<210> SEQ ID NO 66
<211> LENGTH: 71
<212> TYPE: DNA
<213> ORGANISM: Atlantic salmon

<400> SEQUENCE: 66
aggttaatga ttaccaggtt agcatgcgtg agcaaagcat tcactactca tgcgctggga  60
gagcagaaaa t  71

<210> SEQ ID NO 67
<211> LENGTH: 71
<212> TYPE: DNA

<213> ORGANISM: Atlantic salmon

<400> SEQUENCE: 67 ccatctatttt gatagtccttt tccatatttg atagagacat atgccctagg tgaatttaca    60
cattttaagc a    71

<210> SEQ ID NO 68
<211> LENGTH: 71
<212> TYPE: DNA
<213> ORGANISM: Atlantic salmon

<400> SEQUENCE: 68
tttttcattg ccatgccaat tgatctgagt ctccatgttg tcattgcagc aagaggttgc    60
acagtacaga a    71

<210> SEQ ID NO 69
<211> LENGTH: 71
<212> TYPE: DNA
<213> ORGANISM: Atlantic salmon

<400> SEQUENCE: 69
ggtcacatgg cctttgaata aacagcaaaa tacatcctct catgtacaaa tcttccatca    60
gccaaacgct t    71

<210> SEQ ID NO 70
<211> LENGTH: 71
<212> TYPE: DNA
<213> ORGANISM: Atlantic salmon

<400> SEQUENCE: 70 cacgggggc cagtacaaaa aaaaatgcat gaaataaaat ggatgaaatg tatgaattca    60
ctactgtaag t    71

<210> SEQ ID NO 71
<211> LENGTH: 71
<212> TYPE: DNA
<213> ORGANISM: Atlantic salmon

<400> SEQUENCE: 71
acatgaaacg aggggttaat atgataataa gaagggagtt ttaatctata acacacctcg    60
tttattctcc t    71

<210> SEQ ID NO 72
<211> LENGTH: 71
<212> TYPE: DNA
<213> ORGANISM: Atlantic salmon

<400> SEQUENCE: 72
aaaactatac attttggtgg aaggcaaaat cttaaactca tttgagctaa aactcgcaaa    60
tatattggct g    71

<210> SEQ ID NO 73
<211> LENGTH: 71
<212> TYPE: DNA
<213> ORGANISM: Atlantic salmon

<400> SEQUENCE: 73
aagcggttcg atgagtcatt ctggatccaa gccttgtatg agaaactcac agctgcaact    60
ctaagccaaa c    71

<210> SEQ ID NO 74
<211> LENGTH: 71
<212> TYPE: DNA
<213> ORGANISM: Atlantic salmon

<400> SEQUENCE: 74
ctggacaggc tctttggtag tgttcgtgct ctgtggtgac tgttcatctt cagcctggct     60
tggctggtct g                                                          71

<210> SEQ ID NO 75
<211> LENGTH: 71
<212> TYPE: DNA
<213> ORGANISM: Atlantic salmon

<400> SEQUENCE: 75
tttatatctc ttggcggtta ttagttacat tctttgtaaa atgataatag agcacaatat     60
tcacttggct a                                                          71

<210> SEQ ID NO 76
<211> LENGTH: 71
<212> TYPE: DNA
<213> ORGANISM: Atlantic salmon

<400> SEQUENCE: 76
tcaaacgaca tgacgtaaca ggaactacag tagaggaatc ttgtctctgg cctctcagaa     60
ataggttaag t                                                          71

<210> SEQ ID NO 77
<211> LENGTH: 71
<212> TYPE: DNA
<213> ORGANISM: Atlantic salmon

<400> SEQUENCE: 77
atggaaaatg cagcctcatc acagtccact ccagacacct tccctaacgg cagatttcat     60
gagacatatc t                                                          71

<210> SEQ ID NO 78
<211> LENGTH: 71
<212> TYPE: DNA
<213> ORGANISM: Atlantic salmon

<400> SEQUENCE: 78
taaatgcatg tgacctacta caccctccat tgaccactcc tgtaattata tccagccagg     60
tcagtcctta g                                                          71

<210> SEQ ID NO 79
<211> LENGTH: 71
<212> TYPE: DNA
<213> ORGANISM: Atlantic salmon

<400> SEQUENCE: 79
tacactagca tatgaaacca cgtgacaaag aatgaaaagg tgcactcttt agatcatcaa     60
caaaaagatg t                                                          71

<210> SEQ ID NO 80
<211> LENGTH: 71
<212> TYPE: DNA
<213> ORGANISM: Atlantic salmon -continued

<400> SEQUENCE: 80
cctattgaga aaccagttgg gtcattgctt actgagaaac cagtagggac attacctatt    60
gagtaaccag t    71

<210> SEQ ID NO 81
<211> LENGTH: 71
<212> TYPE: DNA
<213> ORGANISM: Atlantic salmon

<400> SEQUENCE: 81
tgttgacaga gtcaggtgca tggcaggtga catacgattg ctccttcaat gcctatatcg    60
tatgtgagat a    71

<210> SEQ ID NO 82
<211> LENGTH: 71
<212> TYPE: DNA
<213> ORGANISM: Atlantic salmon

<400> SEQUENCE: 82
caaaagccac atcaacacaa catgaaggct agatacagat atagtgaaac agaatcttac    60
agtttccatg t    71

<210> SEQ ID NO 83
<211> LENGTH: 71
<212> TYPE: DNA
<213> ORGANISM: Atlantic salmon

<400> SEQUENCE: 83
cagaatgcca tcctgaagga tcttgtgcta cagttcctac tgagaatagt ttcccgccgc    60
ctactggaca g    71

<210> SEQ ID NO 84
<211> LENGTH: 71
<212> TYPE: DNA
<213> ORGANISM: Atlantic salmon

<400> SEQUENCE: 84
tctgttgatg tctatatttg gctaatattc tttttcattt tctgtttcag agtgggcagt    60
ttgactatga c    71

<210> SEQ ID NO 85
<211> LENGTH: 71
<212> TYPE: DNA
<213> ORGANISM: Atlantic salmon

<400> SEQUENCE: 85
agctagagtt gttggtgaca gtaaaggaga aagagaggac cggccagcca tgtgtcagca    60
attgagaaat g    71

<210> SEQ ID NO 86
<211> LENGTH: 71
<212> TYPE: DNA
<213> ORGANISM: Atlantic salmon

<400> SEQUENCE: 86
aatatgcgtg tcacagttcc catttctgag gctgagagat aaacaggcag agataaacag    60
tcacaatggt t    71

```
<210> SEQ ID NO 87
<211> LENGTH: 71
<212> TYPE: DNA
<213> ORGANISM: Atlantic salmon

<400> SEQUENCE: 87
tcccaggtgg cactgataga tgagtacaca ttcccagtag gatcaatgtt tgttcgcacc     60
ctgctattct t                                                          71

<210> SEQ ID NO 88
<211> LENGTH: 71
<212> TYPE: DNA
<213> ORGANISM: Atlantic salmon

<400> SEQUENCE: 88
aggttaatga ttaccaggtt agcatgcgtg agcaaagcat tcactactca tgcgctggga     60
gagcagaaaa t                                                          71

<210> SEQ ID NO 89
<211> LENGTH: 71
<212> TYPE: DNA
<213> ORGANISM: Atlantic salmon

<400> SEQUENCE: 89
gcgctcgcca tagtctcctc attgtgtaac tataatcatg gagaaatatg tgcaacaaca     60
cagttgagac t                                                          71

<210> SEQ ID NO 90
<211> LENGTH: 71
<212> TYPE: DNA
<213> ORGANISM: Atlantic salmon

<400> SEQUENCE: 90
cccgtctgtc agtcattcca tgttcggtgt cattagctga gggctgaagc acggacgttg     60
aacagaagct c                                                          71

<210> SEQ ID NO 91
<211> LENGTH: 71
<212> TYPE: DNA
<213> ORGANISM: Atlantic salmon

<400> SEQUENCE: 91
taaaatggca gttaagtcag cttgtatatt gggtctaaag ataacagtta atgtgctgag     60
gcttgataaa c                                                          71

<210> SEQ ID NO 92
<211> LENGTH: 71
<212> TYPE: DNA
<213> ORGANISM: Atlantic salmon

<400> SEQUENCE: 92
actctgccca aacacacact ctctgtctct gccaggtgat ccagcccct gctcacgcta      60 catcttctcg c                                                          71

<210> SEQ ID NO 93
<211> LENGTH: 71
<212> TYPE: DNA
<213> ORGANISM: Atlantic salmon

<400> SEQUENCE: 93
```

-continued

```
taatctacag ccaatgcaag tacattctgt cgaccgaaga gctctggcca tatcagccct    60
gttatgacca t                                                         71

<210> SEQ ID NO 94
<211> LENGTH: 71
<212> TYPE: DNA
<213> ORGANISM: Atlantic salmon

<400> SEQUENCE: 94
tacacggtac acttgctgca ctatataaaa acactcgggt ccacagcggg agaagaaagt    60
cacggcttta a                                                         71

<210> SEQ ID NO 95
<211> LENGTH: 71
<212> TYPE: DNA
<213> ORGANISM: Atlantic salmon

<400> SEQUENCE: 95
ccagttggga catttcctat tgagaaacca gtcgggatat tacctgttga gaaaccagtt    60
gggacattac c                                                         71

<210> SEQ ID NO 96
<211> LENGTH: 71
<212> TYPE: DNA
<213> ORGANISM: Atlantic salmon

<400> SEQUENCE: 96
ccatctattt gatagtcctt tccatatttg atagagacat atgccctagg tgaatttaca    60
cattttaagc a                                                         71

<210> SEQ ID NO 97
<211> LENGTH: 71
<212> TYPE: DNA
<213> ORGANISM: Atlantic salmon

<400> SEQUENCE: 97
tcgggacgtt gcctattgag aaactaattg ggatattgcc tattgagaag caagttggga    60
cattgcccat t                                                         71

<210> SEQ ID NO 98
<211> LENGTH: 71
<212> TYPE: DNA
<213> ORGANISM: Atlantic salmon

<400> SEQUENCE: 98
ttgagaaaca agttgggata ttgcccgttg agatgctagt tgggacattg cccattgaga    60
aaccagtcgg g                                                         71

<210> SEQ ID NO 99
<211> LENGTH: 71
<212> TYPE: DNA
<213> ORGANISM: Atlantic salmon

<400> SEQUENCE: 99
tgagcgtagt atgacagagt ggtagttagt tgtctcactg accctccgta gctggttggt    60
gaagaacagg g                                                         71

<210> SEQ ID NO 100
<211> LENGTH: 71
```

```
<210> SEQ ID NO 100
<211> LENGTH: 71
<212> TYPE: DNA
<213> ORGANISM: Atlantic salmon

<400> SEQUENCE: 100
ctagttccca cttcacagga gggacattta aaaatacatg caagtgatat gtaaatatga    60
gtaaaagggt t                                                         71

<210> SEQ ID NO 101
<211> LENGTH: 71
<212> TYPE: DNA
<213> ORGANISM: Atlantic salmon

<400> SEQUENCE: 101
cagtacatac aaaactgtag ccaagaatgc atttccgtaa gcttgaatta ctatcatatc    60
agtctttaca g                                                         71

<210> SEQ ID NO 102
<211> LENGTH: 71
<212> TYPE: DNA
<213> ORGANISM: Atlantic salmon

<400> SEQUENCE: 102
ttcaacagat gcctttagcc caagctgatg aaacgaatac agatgccatc attggggcag    60
attaaacatg t                                                         71

<210> SEQ ID NO 103
<211> LENGTH: 71
<212> TYPE: DNA
<213> ORGANISM: Atlantic salmon

<400> SEQUENCE: 103
tcagttttct caagtgtctg tctgaccgtg tcgttgtcaa accagttcca gatcgcaggc    60
cttggaagcc g                                                         71

<210> SEQ ID NO 104
<211> LENGTH: 71
<212> TYPE: DNA
<213> ORGANISM: Atlantic salmon

<400> SEQUENCE: 104
caacagccta gcccaaggct gtccaacccc gttcctggag agctaacatc agcccgctgc    60
ctggctagtg t                                                         71

<210> SEQ ID NO 105
<211> LENGTH: 71
<212> TYPE: DNA
<213> ORGANISM: Atlantic salmon

<400> SEQUENCE: 105
cctcccccaa tgccaaatgc ctcatatctg ttggaacctc cacagagaat ggcatctgaa    60
aaacatgttt a                                                         71

<210> SEQ ID NO 106
<211> LENGTH: 71
<212> TYPE: DNA
<213> ORGANISM: Atlantic salmon

<400> SEQUENCE: 106
gcagcactga tgaaggcatt gaagcctttt gttaatattt tgagcatggg tttaattaag    60
```

```
tacatttttg c                                                          71

<210> SEQ ID NO 107
<211> LENGTH: 71
<212> TYPE: DNA
<213> ORGANISM: Atlantic salmon

<400> SEQUENCE: 107
tcctcttcaa attggacaca agtcttcgtc ctcatttctc tctgcatctt cattttcctc     60
cttctctgaa t                                                          71

<210> SEQ ID NO 108
<211> LENGTH: 71
<212> TYPE: DNA
<213> ORGANISM: Atlantic salmon

<400> SEQUENCE: 108
ggttgtttcc caaacataaa ttgatatgga gagtcatgtc atttcgtgtc atttcttgtg     60
caattatatg c                                                          71

<210> SEQ ID NO 109
<211> LENGTH: 71
<212> TYPE: DNA
<213> ORGANISM: Atlantic salmon

<400> SEQUENCE: 109
atggcagcaa gtagggtgga cgaaatggag gacattgaga aaaagctggt gaagcagcag     60
ctgtgctgga a                                                          71

<210> SEQ ID NO 110
<211> LENGTH: 71
<212> TYPE: DNA
<213> ORGANISM: Atlantic salmon

<400> SEQUENCE: 110
caaacatcaa atatccgtgc taaatgaaat ggcaaactaa cataaattag cttgatcgtt     60
taataagtac t                                                          71

<210> SEQ ID NO 111
<211> LENGTH: 71
<212> TYPE: DNA
<213> ORGANISM: Atlantic salmon

<400> SEQUENCE: 111
aggcaccata agactccaag aggacactaa cagctagtga aaaacatgga cctgggtcct     60
gttatccttg t                                                          71

<210> SEQ ID NO 112
<211> LENGTH: 71
<212> TYPE: DNA
<213> ORGANISM: Atlantic salmon

<400> SEQUENCE: 112
ggttcggggg agctgtgtta ccgtgcactg tctatatcag attgctaaat aattaccatg     60
actgcttctg a                                                          71

<210> SEQ ID NO 113
<211> LENGTH: 71
<212> TYPE: DNA
<213> ORGANISM: Atlantic salmon
```

<400> SEQUENCE: 113
aacagcagtg ccagagaagg aactttacat ttaatataat tctgagtcat taacatttgg    60
ctggacggtg t                                                          71

<210> SEQ ID NO 114
<211> LENGTH: 71
<212> TYPE: DNA
<213> ORGANISM: Atlantic salmon

<400> SEQUENCE: 114
agggtataga tgggctcatg accatgacct ccaccgttac ctttaccgcc tccctccgcc    60
atcacgggct g                                                          71

<210> SEQ ID NO 115
<211> LENGTH: 71
<212> TYPE: DNA
<213> ORGANISM: Atlantic salmon

<400> SEQUENCE: 115
tgaaaaggcg taggagagag aagcgaagag acagaaaaaa tacgctaata tcaggtgttg    60
ttctgagttt c                                                          71

<210> SEQ ID NO 116
<211> LENGTH: 71
<212> TYPE: DNA
<213> ORGANISM: Atlantic salmon

<400> SEQUENCE: 116
caacaggaga taaacccctc tactgtgcag cagggaagaa cagatattca caatcagggc    60
tgcaatacag a                                                          71

<210> SEQ ID NO 117
<211> LENGTH: 71
<212> TYPE: DNA
<213> ORGANISM: Atlantic salmon

<400> SEQUENCE: 117
ctgtctgtcc actaaatcac tggatatata tatgacgggc tgacgggaca ggacagggag    60
acatatgagg g                                                          71

<210> SEQ ID NO 118
<211> LENGTH: 71
<212> TYPE: DNA
<213> ORGANISM: Atlantic salmon

<400> SEQUENCE: 118
ttccatgatg taacttaaga tgccccactg tgtagttgga aagagtgatg agatgtgggc    60
aagaaaagta g                                                          71

<210> SEQ ID NO 119
<211> LENGTH: 71
<212> TYPE: DNA
<213> ORGANISM: Atlantic salmon

<400> SEQUENCE: 119
taaaatcatg gggacggtct ctgagaaaat gcactgaaca aaccaatact attttttttt    60
tcatattgca a                                                          71

-continued

```
<210> SEQ ID NO 120
<211> LENGTH: 71
<212> TYPE: DNA
<213> ORGANISM: Atlantic salmon

<400> SEQUENCE: 120
actagaaatt atgcaagcag attgacttaa taccattctg gcctataggg ttgttttttt      60
attcagacat g                                                          71

<210> SEQ ID NO 121
<211> LENGTH: 71
<212> TYPE: DNA
<213> ORGANISM: Atlantic salmon

<400> SEQUENCE: 121
agcctccagg ttggtctcag ggtttaagac ctacctttca ttctgaatag cctccaggtt      60
ggcacggctg t                                                          71

<210> SEQ ID NO 122
<211> LENGTH: 71
<212> TYPE: DNA
<213> ORGANISM: Atlantic salmon

<400> SEQUENCE: 122
gctggcctgc ttctcctcgt cctcatctgg ctgtgtgcag cggagtgtgt aagtagccta      60
atccacctga a                                                          71

<210> SEQ ID NO 123
<211> LENGTH: 71
<212> TYPE: DNA
<213> ORGANISM: Atlantic salmon

<400> SEQUENCE: 123
agccaagaaa aaaactgcaa ttttattaat agtttaaaag aagctccata gttcatgaaa      60
acattgtttt c                                                          71

<210> SEQ ID NO 124
<211> LENGTH: 71
<212> TYPE: DNA
<213> ORGANISM: Atlantic salmon

<400> SEQUENCE: 124
agctagagtt gttggtgaca gtaaaggaga aagagaggac cggccagcca tgtgtcagca      60
attgagaaat g                                                          71

<210> SEQ ID NO 125
<211> LENGTH: 71
<212> TYPE: DNA
<213> ORGANISM: Atlantic salmon

<400> SEQUENCE: 125
cggctgtaca aagatcgtct gaaggtcaca ggcggattga actctgacct gctcaacgtg      60
accatagccc a                                                          71

<210> SEQ ID NO 126
<211> LENGTH: 71
<212> TYPE: DNA
<213> ORGANISM: Atlantic salmon

<400> SEQUENCE: 126
```

```
gcacttgtta gcctagccta gtttagccta gcctcagaga tagatgcttg tggatttccc      60
tcaggcagaa t                                                           71

<210> SEQ ID NO 127
<211> LENGTH: 20
<212> TYPE: DNA
<213> ORGANISM: Artificial Sequence
<220> FEATURE:
<223> OTHER INFORMATION: Atlantic salmon cd8 alpha chain forward primer

<400> SEQUENCE: 127
tcgtgcaaag tgggaaaggt                                                  20

<210> SEQ ID NO 128
<211> LENGTH: 20
<212> TYPE: DNA
<213> ORGANISM: Artificial Sequence
<220> FEATURE:
<223> OTHER INFORMATION: Atlantic salmon cd8 alpha chain reverse primer

<400> SEQUENCE: 128
ggtgcccaaa cgatcaaatc                                                  20

<210> SEQ ID NO 129
<211> LENGTH: 16
<212> TYPE: DNA
<213> ORGANISM: Artificial Sequence
<220> FEATURE:
<223> OTHER INFORMATION: TaqMan probe
<220> FEATURE:
<221> NAME/KEY: misc_feature
<222> LOCATION: (1)..(1)
<223> OTHER INFORMATION: FAM
<220> FEATURE:
<221> NAME/KEY: misc_feature
<222> LOCATION: (16)..(16)
<223> OTHER INFORMATION: MGB

<400> SEQUENCE: 129
accctactgc atcctg                                                      16

<210> SEQ ID NO 130
<211> LENGTH: 20
<212> TYPE: DNA
<213> ORGANISM: Artificial Sequence
<220> FEATURE:
<223> OTHER INFORMATION: housekeeping gene elf1a forward primer

<400> SEQUENCE: 130
tgcccctcca ggatgtctac                                                  20

<210> SEQ ID NO 131
<211> LENGTH: 18
<212> TYPE: DNA
<213> ORGANISM: Artificial Sequence
<220> FEATURE:
<223> OTHER INFORMATION: housekeeping gene elf1a reverse primer

<400> SEQUENCE: 131
cacggcccac aggtactg                                                    18

<210> SEQ ID NO 132
<211> LENGTH: 17
<212> TYPE: DNA
<213> ORGANISM: Artificial Sequence
<220> FEATURE:
```

```
<223> OTHER INFORMATION: TaqMan probe
<220> FEATURE:
<221> NAME/KEY: misc_feature
<222> LOCATION: (1)..(1)
<223> OTHER INFORMATION: VIC
<220> FEATURE:
<221> NAME/KEY: misc_feature
<222> LOCATION: (17)..(17)
<223> OTHER INFORMATION: MGB

<400> SEQUENCE: 132
ccaataccgc cgatttt                                                  17
```